US012793848B2

(12) United States Patent
Ackerman et al.

(10) Patent No.: US 12,793,848 B2
(45) Date of Patent: Nov. 10, 2026

(54) SYSTEMS AND METHODS FOR CLASSIFYING STORAGE LOWER URINARY TRACT SYMPTOMS

(71) Applicant: CEDARS-SINAI MEDICAL CENTER, Los Angeles, CA (US)

(72) Inventors: A. Lenore Ackerman, Los Angeles, CA (US); Kai B. Dallas, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 624 days.

(21) Appl. No.: 17/547,119

(22) Filed: Dec. 9, 2021

(65) Prior Publication Data

US 2022/0181027 A1 Jun. 9, 2022

Related U.S. Application Data

(60) Provisional application No. 63/123,205, filed on Dec. 9, 2020.

(51) Int. Cl.

| | |
|---|---|
| ***G16H 50/20*** | (2018.01) |
| ***A61B 5/00*** | (2006.01) |
| ***A61B 5/20*** | (2006.01) |
| ***G16H 10/20*** | (2018.01) |
| ***G16H 50/30*** | (2018.01) |

(52) U.S. Cl.

CPC ............. *G16H 50/20* (2018.01); *A61B 5/202* (2013.01); *A61B 5/7267* (2013.01); *A61B 5/7475* (2013.01); *G16H 10/20* (2018.01); *G16H 50/30* (2018.01)

(58) Field of Classification Search

CPC ................................................ G06Q 50/20–26

See application file for complete search history.

(56) References Cited

U.S. PATENT DOCUMENTS

| | | | | |
|---|---|---|---|---|
| 2004/0138924 | A1* | 7/2004 | Pristine | G06Q 10/04 705/2 |
| 2020/0121236 | A1* | 4/2020 | Gao | G16H 10/60 |
| 2020/0143922 | A1* | 5/2020 | Chekroud | G16H 20/10 |
| 2020/0268302 | A1* | 8/2020 | Oh | A61B 5/227 |

OTHER PUBLICATIONS

Zhao M, Tang Y, Kim H, Hasegawa K. Machine Learning With K-Means Dimensional Reduction for Predicting Survival Outcomes in Patients With Breast Cancer. Cancer Informatics. 2018;17. (Year: 2018).*

(Continued)

*Primary Examiner* — Jordan L Jackson

(74) *Attorney, Agent, or Firm* — Nixon Peabody LLP

(57) ABSTRACT

Systems and methods are disclosed for diagnosis and treatment of urinary tract symptoms into machine learning based clusters. In some examples, a diagnostic questionnaire is processed by a machine learning model to evaluate a patient's urinary tract health condition and determine a diagnosis based on one or more indications of urinary tract health of the patient. In one example, the machine learning model is trained using datasets labelled according to one or more diagnostic clusters generated by an unsupervised learning model, such as a clustering model. In some examples, a measure of severity of the diagnosis is output by the machine learning model or a second machine learning model.

26 Claims, 10 Drawing Sheets

(56) References Cited

OTHER PUBLICATIONS

H. H. Lai, J. Vetter, S. Jain, R.W. Gereau, G.L. Andriole. The overlap and distinction of self-reported symptoms between interstitial cystitis/bladder pain syndrome and overactive bladder: a questionnaire based analysis. J Urol, 192 (2014), pp. 1679-1685 (Year: 2014).*

Paul, R., Andlauer, T.F.M., Czamara, D. et al. Treatment response classes in major depressive disorder identified by model-based clustering and validated by clinical prediction models. Transl Psychiatry 9, 187 (2019) (Year: 2019).*

Andreev VP, Liu G, Yang CC, et al. Symptom Based Clustering of Women in the LURN Observational Cohort Study. J Urol. 2018; 200(6):1323-1331. (Year: 2018).*

Wang Bao, Ning Lianju, Kong Yue, Integration of unsupervised and supervised machine learning algorithms for credit risk assessment, Expert Systems with Applications, vol. 128, 2019, pp. 301-315, ISSN 0957-4174 (Year: 2019).*

Fall et al., EAU Guidelines on Chronic Pelvic Pain, 46 European Urology 681-689 (Year: 2004).*

Santana et al., Chronic Pain Diagnosis Using Machine Learning, Questionnaires, and QST: A Sensitivity Experiment, 10 Diagnostics (Nov. 17, 2020) (Year: 2020).*

Ackerman AL, Lai HH, Parameshwar PS, Eilber KS, Anger JT. Symptomatic overlap in overactive bladder and Interstitial cystitis/bladder pain syndrome:development of a new algorithm. BJU Int. Apr. 2019;123(4):682-693.

Adamson AS, Welch HG. Machine Learning and the Cancer-Diagnosis Problem—No Gold Standard. N Engl J Med. Dec. 12, 2019;381(24):2285-2287.

Awan SE, Sohel F, Sanfilippo FM, Bennamoun M, Dwivedi G. Machine learning in heart failure: ready for prime time. Curr Opin Cardiol. Mar. 2018;33(2):190-195.

Biasi G, Di Sabatino V, Ghizzani A, Galeazzi M. Chronic pelvic pain: comorbidity between chronic musculoskeletal pain and vulvodynia. Reumatismo. Jun. 6, 2014;66(1):87-91.

Clemens JQ, Mullins C, Ackerman AL, Bavendam T, van Bokhoven A, Ellingson BM, Harte SE, Kutch JJ, Lai HH, Martucci KT, Moldwin R, Naliboff BD, Pontari MA, Sutcliffe S, Landis Jr; Mapp Research Network Study Group. Urologic chronic pelvic pain syndrome: insights from the MAPP Research Network. Nat Rev Urol. Mar. 2019;16(3):187-200.

Choo MS, Uhmn S, Kim JK, Han JH, Kim DH, Kim J, Lee SH. A Prediction Model Using Machine Learning Algorithm for Assessing Stone-Free Status after Single Session Shock Wave Lithotripsy to Treat Ureteral Stones. J Urol. Dec. 2018;200(6):1371-1377.

Coyne KS, Sexton CC, Thompson CL et al. The prevalence of lower urinary tract symptoms (LUTS) in the USA, the JK and Sweden: results from the Epidemiology of LUTS (EpiLUTS) study. BJU Int 2009; 104: 352-60.

Coyne KS, Wein A, Nicholson S, Kvasz M, Chen CI, Milsom I. Economic burden of urgency urinary incontinence in the United States: a systematic review. J Manag Care Pharm 2014; 20: 130-40.

Erickson BJ, Korfiatis P, Akkus Z, Kline TL. Machine Learning for Medical Imaging. Radiographics. Mar.-Apr. 2017;37(2):505-515.

Goldenberg SL, Nir G, Salcudean SE. A new era: artificial intelligence and machine learning in prostate cancer. Nat Rev Urol. Jul. 2019;16(7):391-403.

Gormley EA, Lightner DJ, Burgio KL et al. Diagnosis and treatment of overactive bladder (non-neurogenic) in adults: AUA/SUFU guideline. J Urol 2012; 188: 2455-63.

Hanno PM, Burks DA, Clemens JQ et al. AUA guideline for the diagnosis and treatment of interstitial cystitis/bladder pain syndrome. J Urol 2011; 185: 2162-70.

Hasnain Z, Mason J, Gill K, Miranda G, Gill IS, Kuhn P, Newton PK. Machine learning models for predicting post-cystectomy recurrence and survival in bladder cancer patients. PLoS One. Feb. 20, 2019;14(2).

Karmonik C, Boone T, Khavari R. Data-Driven Machine-Learning Quantifies Differences in the Voiding Initiation Network in Neurogenic Voiding Dysfunction in Women With Multiple Sclerosis. Int Neurourol J. Sep. 2019;23(3):195-204.

Kocak B, Yardimci AH, Bektas CT, Turkcanoglu MH, Erdim C, Yucetas U, Koca SB, Kilickesmez O. Textural differences between renal cell carcinoma subtypes:Machine learning-based quantitative computed tomography texture analysis with independent external validation. Eur J Radiol. Oct. 2018;107:149-157.

Lai HH, Vetter J, Jain S, Gereau RW, Andriole GL. The overlap and distinction of self-reported symptoms between interstitial cystitis/bladder pain syndrome and overactive bladder: a questionnaire based analysis. J Urol 2014; 192: 1679-86.

Milsom I, Kaplan SA, Coyne KS, Sexton CC, Kopp ZS. Effect of bothersome overactive bladder symptoms on health-related quality of life, anxiety, depression, and treatment seeking in the United States: results from EpiLUTS. Urology 2012; 80: 90-6.

Obermeyer Z, Emanuel EJ. Predicting the Future—Big Data, Machine Learning, and Clinical Medicine. N Engl J Med. Sep. 29, 2016;375(13):1216-9.

Ozkan IA, Koklu M, Sert IU. Diagnosis of urinary tract infection based on artificial intelligence methods. Comput Methods Programs Biomed. Nov. 2018;166:51-59.

Sheyn D, Ju M, Zhang S, Anyaeche C, Hijaz A, Mangel J, Mahajan S, Conroy B, El-Nashar S, Ray S. Development and Validation of a Machine Learning Algorithm for Predicting Response to Anticholinergic Medications for Overactive Bladder Syndrome. Obstet Gynecol. Nov. 2019;134(5):946-957.

Suarez-Ibarrola R, Hein S, Reis G, Gratzke C, Miernik A. Current and future applications of machine and deep learning in urology: a review of the literature on urolithiasis, renal cell carcinoma, and bladder and prostate cancer. World J Urol. Nov. 5, 2019.

Thu JHL, Vetter J, Lai HH. The Severity and Distribution of Nonurologic Pain and Urogenital Pain in Overactive Bladder are Intermediate Between Interstitial Cystitis and Controls. Urology. Aug. 2019;130:59-64.

Wolff BJ, Joyce CJ, Brincat CA, Mueller ER, Fitzgerald CM. Pelvic floor myofascial pain in patients with symptoms of urinary tract infection. Int J Gynaecol Obstet. May 2019;145(2):205-211.

* cited by examiner

500

| Cluster | Salient Features | Most common Pre-Referral Diagnosis | New Diagnostic Classification |
|---|---|---|---|
| 1 (n=142) | Asymptomatic on all indices | Microscopic Hematuria | Asymptomatic Controls |
| 2 (n=85) | High responses to all questionnaire areas | Interstitial Cystitis/Bladder Pain Syndrome | Bladder Pain Syndrome (BPS) |
| 3 (n=111) | Pain at vagina and urethra. Elevated VAS Pain | Interstitial Cystitis/Bladder Pain Syndrome | Non-Urologic Urogenital Pain (NUPP) |
| 4 (n=121) | Urgency, storage symptoms without incontinence | Overactive bladder. Interstitial Cystitis/Bladder Pain Syndrome | Pelvic Floor Dysfunction |
| 5 (n= 55) | Leakage with no warning. Frequency. Nocturia. Fear of leakage impacts quality of life. | Overactive bladder | Urgency Urinary Incontinence (UUI) |

FIG. 5B

SYSTEMS AND METHODS FOR CLASSIFYING STORAGE LOWER URINARY TRACT SYMPTOMS

CROSS-REFERENCE TO RELATED APPLICATIONS

This application claims benefit under 35 U.S.C. § 119(e) of U.S. Provisional Application No. 63/123,205 filed Dec. 9, 2020, the contents of which are incorporated herein by reference in its entirety.

FIELD

The present invention is directed to diagnostic and treatment systems and methods relating to urinary tract symptoms.

BACKGROUND

The following description includes information that may be useful in understanding the present invention. It is not an admission that any of the information provided herein is prior art or relevant to the presently claimed invention, or that any publication specifically or implicitly referenced is prior art.

Lower urinary track symptoms (LUTS) form a set of complex and poorly understood symptoms that encompass problems with normal holding of urine (storage) and bladder emptying (voiding). The storage subset of LUTS include: urinary urgency, frequency, nocturia, painful urination, and bladder discomfort. These disorders are frequently chronic and debilitating, and negatively impact a patient's quality of life.

SUMMARY

Methods and systems are provided for classifying lower urinary tract symptoms into novel diagnostic categories using machine learning algorithms. The storage subset of LUTS, including urinary urgency, frequency, nocturia, painful urination, and bladder discomfort, contributes to a heavy burden of illness and are categorized into several conditions with sizable symptomatic overlap (e.g. interstitial cystitis/painful bladder syndrome (IC/BPS) and overactive bladder (OAB)). These disorders are frequently chronic and debilitating, and negatively impact a patient's quality of life. Further, these disorders represent a significant economic burden, with an estimate annual cost to the health care system in excess of 80 billion dollars per year. Compounding this is the fact that appropriate diagnosis and treatment is hampered by the challenges in identifying and classifying these conditions.

Two syndromes, IC/BPS and OAB, present particular diagnostic challenges as there are currently no definitive tests or markers available. Diagnosis is thus based on subjective patient-reported symptoms. IC/BPS is characterized by bladder pain while the key symptom of OAB is urinary urgency. Although these two conditions are classically considered distinct entities, recent evidence suggests there is actually significant symptomatic overlap between them. As a result, clinical dilemmas develop in diagnosing storage LUTS, which reduce effective patient care.

Further, previous approaches for evaluating patients with LUTS require an intermediate specialist to make a diagnosis based on the symptoms presented. The patient is then referred a specialist for final diagnosis and treatment. As a result, there is significant delay in care provided to the patient. Further, due to symptomatic overlap, the disease condition is not diagnosed accurately.

In order to at least partially address the above-mentioned issues, the inventors herein provide systems and methods for diagnosing lower urinary tract symptoms. In one example, a method for diagnosing lower urinary tract symptoms comprises: receiving patient data via an input device, the input device including a user interface configured to receive patient responses to one or more questionnaires regarding urinary tract health symptoms; process the patient data via a trained machine learning algorithm to output a urinary tract health diagnosis based on the lower urinary tract symptoms; and output the urinary tract health diagnosis via the user interface; wherein the trained machine learning algorithm is trained to categorize the patient data into one disease category of one or more urinary tract disease categories. In one example, the trained machine learning algorithm outputs a severity level classification based on the one disease category; wherein the trained machine learning algorithm is further trained to output a severity level classification based on the one disease category.

In this way, by automatically determining a urinary tract disease category using trained machine learning algorithms, more accurate and quick diagnosis is achieved. As a result, patient may receive appropriate treatment more quickly, which prevents or slows disease progression, and allows the patient to return to full engagement in society. Further, by improving accuracy in diagnosis and treating or ameliorating the disease, the patients not only have better overall quality of life, but can engage more fully in society, lose less productive work time. Furthermore, through more accurate diagnosis, treatment management is improved, for example through effective follow-up diagnosis, which in turn reduces chances of institutionalization (e.g., nursing home) of older individuals.

As one example, a machine learning model may include an unsupervised learning model. The unsupervised learning model may be trained according to a clustering algorithm to receive a plurality of patient response datasets and categorize patient data into a number of urinary tract disease clusters based on one or more of the symptoms and severity of the lower urinary tract symptoms in the patient response datasets. In one example, a k-means clustering technique may be used to generate the number of urinary tract disease clusters and group the patient response datasets. Further, a supervised classification algorithm, such as a random forest algorithm, is trained on the number of urinary tract clusters to classify patients into one of the number of urinary tract disease clusters. Thus, when new patient data is received (e.g., based on patient responses to questionnaires and/or demographic data), the machine learning model may categorize the new patient data into one of the urinary tract disease clusters, and output a diagnosis of urinary tract health condition based on the category into which the new patient data is placed. Further, experimental results that validate these novel diagnostic groupings are also discussed herein.

Further, in some examples, the machine learning model may further include another supervised learning model for each of the number of urinary tract disease clusters. The supervised learning model may be trained to classify the diagnosed urinary tract health condition according to a severity level of the disease. For example, upon identifying the disease category for the new patient data, the patient data may be input into a supervised learning model corresponding to the identified disease category, and a severity level of the disease may be generated as output. In one example, a classification model may be implemented to classify the severity level of the disease category. In another example a regression model may be implemented to generate a score indicative of the severity level of the disease category. In yet another example, a classification model and a regression model may be implemented. In some embodiments, the supervised learning model may be a random forest model. However, it will be appreciated that other supervised learning models, such a support vector machine, k-nearest neighbor, convoluted neural networks, etc., may be used.

In this way, by utilizing an unsupervised learning algorithm, novel diagnostic groupings for lower urinary tract symptoms are identified. The novel diagnostic groupings enable clinicians to quickly diagnose urinary tract diseases and provide appropriate treatment, thereby significantly improving patient outcome. Further, in some examples, the machine learning model outputs a diagnostic grouping as well as a severity of the diagnosed condition. Thus, severity of the diagnosed condition may be monitored to evaluate patient response to a treatment. As a result, follow-up care is improved.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 5B shows a table of feature descriptions corresponding to diagnostic classifications generated by the machine learning algorithm and pre-referral diagnosis without using the machine learning algorithm;

Figure 1:
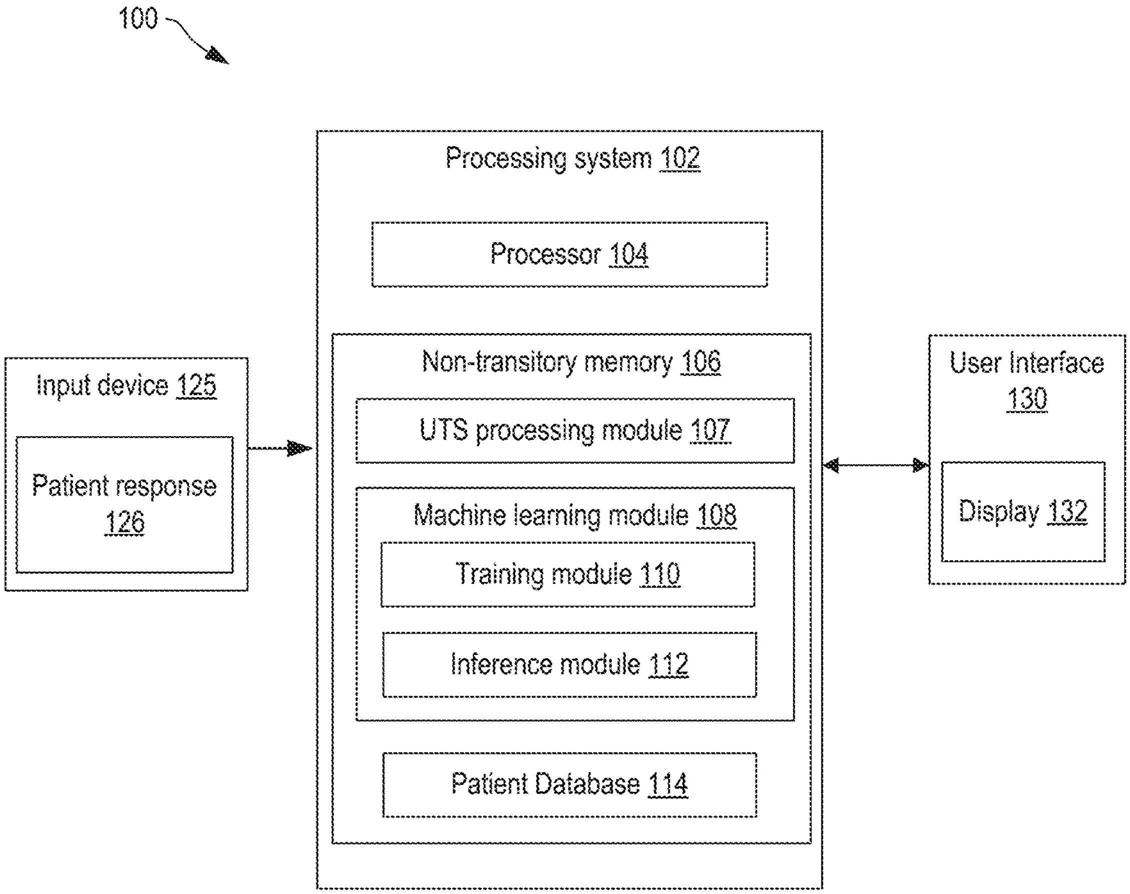
FIG. 1 shows a block diagram of a urinary tract health processing system for implementing a machine learning model for urinary tract health evaluation, according to an embodiment of the disclosure.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Definitions

As used herein, the term "random forest model" refers to a classifier that is based a number of decision trees that operate as an ensemble. The decision trees may be trained with a variety of methods, including the bagging method. In some examples, the decision trees may be built within random input observations (e.g. random input features based on demographic data and/or patient questionnaire responses).

As used herein, the term "patient questionnaire" refers to a questionnaire administered to a patient to assess patient symptoms. Examples of these include:

Interstitial Cystitis Symptom and Problem Indices (ICSI/ICPI)

Overactive Bladder Questionnaire (OABq)

Genitourinary Pain Index (GUPI)

Pelvic Floor Disability Index (PFDI-20)

The content of each of these questionnaires is incorporated by reference in their entirety. For instance, each of the questionnaires may have a set of textual questions such as "how many times a day do you go to the bathroom" and allow the patient to answer 0, 1, 2, 3, or, 4, where "0" is 3-6 times, "1" is 7-10 times, "2" is 11-14 times, "3" is 15-19 times, and "4" is 20+ times a day. In this example, each of the questions may have an answer that is categorized as 0, 1, 2, 3, or 4. Once a patient is finished with the questionnaire, the patient may have a total score added up from all of the answers for that particular questionnaire. In some examples, some of the questions will contribute to a symptom score and some will contribute to a "bother score." Accordingly, other examples of questions may be administered, and the foregoing is just one example.

The term "subject" refers to a mammal, such as a human or an animal. The mammal can be a human, non-human primate, mouse, rat, dog, cat, horse, or cow, but is not limited to these examples. Mammals other than humans can be advantageously used as subjects that represent animal models of, for example, urinary tract disease.

A subject can be one who has been previously diagnosed with or identified as suffering from or having a condition in need of treatment of a disease or disorder as described herein (e.g., an urinary tract disease) or one or more complications related to such a condition, and optionally, have already undergone treatment for a disease or disorder as described herein (e.g., a urinary tract disease) or the one or more complications related to a disease or disorder as described herein (e.g., a urinary tract disease). Alternatively, a subject can also be one who has not been previously diagnosed as having a disease or disorder as described herein (e.g., a urinary tract disease) or one or more complications related to a disease or disorder as described herein (e.g., a urinary tract disease). For example, a subject can be one who exhibits one or more risk factors for a disease or disorder as described herein (e.g., a urinary tract disease) or one or more complications related to a disease or disorder as described herein (e.g., a urinary tract disease) or a subject who does not exhibit risk factors.

A "subject in need" of treatment for a particular condition can be a subject having that condition, diagnosed as having that condition, or at risk of developing that condition.

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

Overview

Lower urinary track symptoms (LUTS) form a set of complex and poorly understood symptoms that encompass problems with normal holding of urine (storage) and bladder emptying (voiding). The storage subset of LUTS includes: urinary urgency, frequency, nocturia, painful urination, and bladder discomfort. These disorders are frequently chronic and debilitating, and negatively impact a patient's quality of life.

Appropriate diagnosis and treatment are hampered by the challenges in identifying and classifying the underlying conditions that cause the symptoms above. For instance, two syndromes, IC/BPS and OAB, present particular diagnostic challenges as there are currently no definitive tests or markers available. Diagnosis is thus based on subjective patients reported symptoms. Although these two conditions are classically considered distinct entities, recent evidence suggests significant symptomatic overlap between them.

Accordingly, disclosed herein are system and methods for diagnosing and treating patients by classifying the patient's responses to questionnaires using a machine learning algorithm to output a diagnosis and/or treatment. In some examples, diagnostic clusters are formed using a k-means clustering algorithm based on patient responses to urinary tract questionnaires and demographic data. These diagnostic clusters are then used to build a random forest algorithm to classify future patients in order to optimize their treatments.

In some examples, an unsupervised clustering method is applied to patient responses to questionnaires to develop diagnostic clusters in an unsupervised manner. In some examples, the disclosed systems and methods may identify distinct diagnostic clusters that are more accurate than physician applied diagnostic labels.

The technical effect of implementing a machine learning model trained according to an unsupervised algorithm for classifying symptoms corresponding to lower urinary tract health includes generation of novel diagnostic categories. The novel diagnostic categories improve accuracy and efficiency of diagnosis of urinary tract health symptoms. In particular, when syndromes are present with overlapping symptoms, the novel diagnostic categories provide improvement in diagnosing urinary tract diseases. Further, the machine learning model enables faster diagnosis of classifying patient symptoms into the diagnostic categories, which enables a specialist to recommend appropriate treatment regimen. Further still, the machine learning model may include a supervised learning model that facilitates classification of severity levels (e.g., multi-class classification), which improves evaluation of effectiveness of treatment, and appropriate update of the treatment regimen. Thus, follow-up care is improved. Thus, overall, the systems and methods provided herein provide significant improvement in the field of urinary tract health by improving accuracy and efficiency of diagnosis of urinary track symptoms.

System

FIG. 1 shows a processing system 102 that may be implemented for evaluating urinary tract health conditions. In one embodiment, the processing system 102 may be incorporated into a computing device, such as a workstation at a health care facility. The processing system 102 is communicatively coupled to an input device 125. The input device 125 may be a computing device configured to receive one or more patient responses 126. An example of the computing device is shown and described with respect to FIG. 2. Briefly, the computing device may include one or more processors and one or more memory units. Further, the computing device may receive responses to a questionnaire from a patient, via an input unit. The input unit may be a text input unit (e.g., keyboard), a voice input unit (e.g., microphone), or a combination thereof, for example.

The processing system 102 may receive data from the input device 125. In one example, the processing system 102 may receive data from a storage device which stores the data generated by these modalities. In another embodiment, the processing system 102 may be disposed at a device (e.g., edge device, server, etc.) communicatively coupled to a computing system that may receive data from the plurality of sensors and/or systems, and transmit the plurality of data modalities to the device for further processing. The processing system 102 includes a processor 104, a user interface 130, which, in some aspects, may be a user input device, and display 132.

Non-transitory memory 106 may store a UTS processing module 107. In one example, the UTS processing module 107 may receive patient data, including patient response data (e.g., patient response to questionnaires) data and demographics data (e.g., age, weight, height) and pre-process the data before passing through the machine learning module 108 for urinary tract health evaluation.

Figure 2:
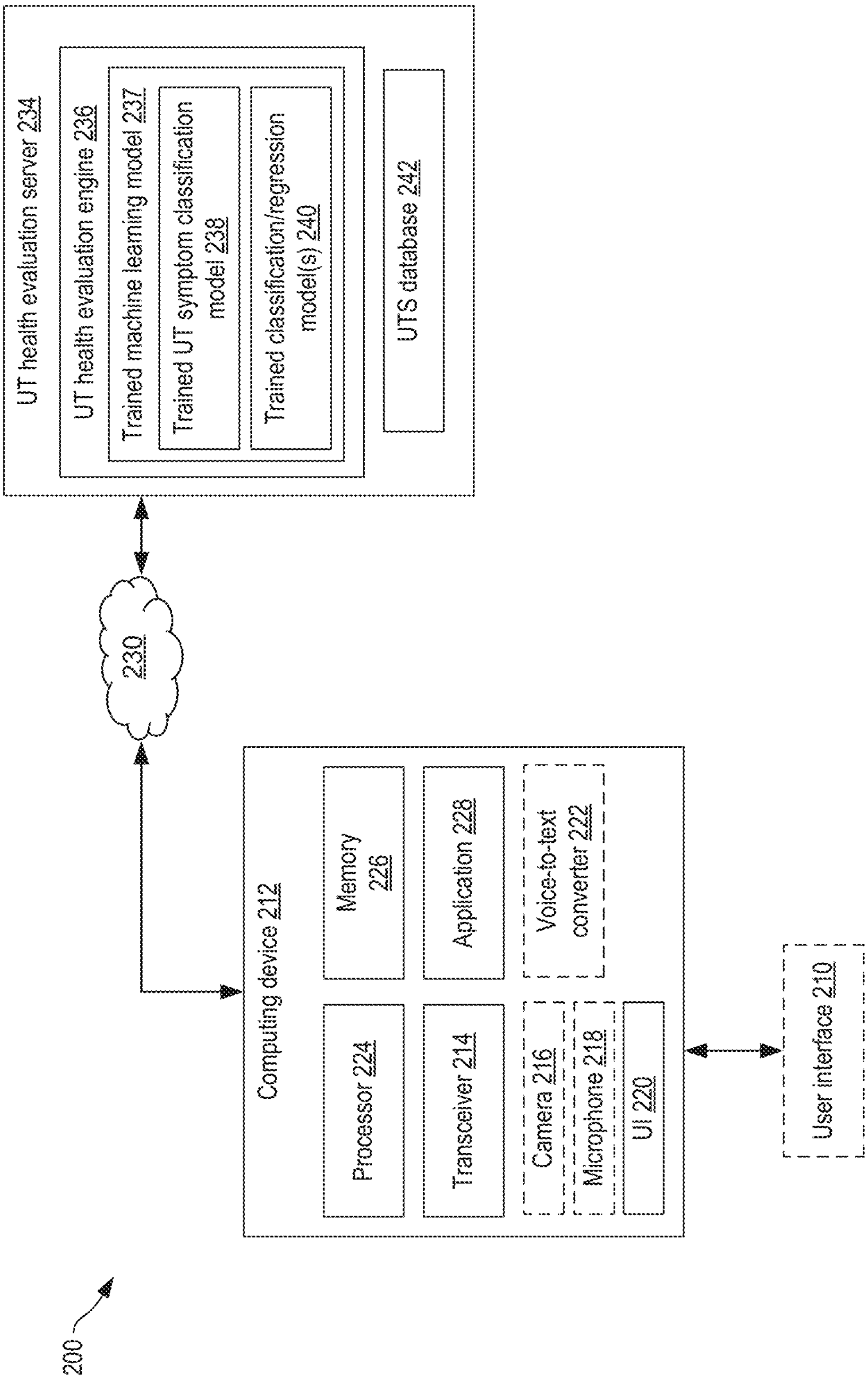
FIG. 2 shows a block diagram of a urinary tract health evaluation system including a trained machine learning model, according to an embodiment of the disclosure.

Non-transitory memory 106 may store a machine learning module 108. The multi-modal machine learning module 108 may include a machine learning model that is trained for evaluating a urinary tract (UT) health condition using patient data. Components of the machine learning model are shown at FIG. 2. Accordingly, the machine learning module 108 may include instructions for receiving modality data from the input device 125, and implementing the machine learning model for evaluating a urinary tract health condition of a patient. An example server side implementation of the machine learning model for urinary tract health condition evaluation is discussed below at FIG. 2.

Non-transitory memory 106 may further store training module 110, which includes instructions for training the machine learning model stored in the machine learning module 108. Training module 110 may include instructions that, when executed by processor 104, cause UT health processing system 102 to train one or more subnetworks in the machine learning model. Example protocols implemented by the training module 110 may include unsupervised learning techniques such as clustering techniques (e.g., hierarchical clustering, k-means clustering, mixture models, etc.) and neural network techniques (e.g., autoencoders, generative adversarial networks, self-organizing maps (SOM), etc.) such that the machine learning model can be trained and can classify input data that were not used for training. Further, the training module 110 may also implement supervised learning techniques, such as random forest, logistic regression, support vector machine, convoluted neural networks, such that the machine learning model can be trained on labelled datasets (e.g., datasets labelled based on clusters obtained from the unsupervised algorithm) and can generate a classification output (e.g., classification of urinary tract symptoms into one of a number of disease categories, multi-level classification of disease severity, etc.)

Non-transitory memory 106 also stores an inference module 112 that comprises instructions for testing new data with the trained machine learning model. Further, non-transitory memory 106 may store patient data 114, such as patient data received from the input device 125. In some examples, the patient data may include patient demographic data and/or electronic health record (EHR) data from an EHR database. In some examples, the patient data 114 may include a plurality of training datasets for the machine learning model.

Processing system 102 may further include user interface 130. User interface 130 may be a user input device, and may comprise one or more of a touchscreen, a keyboard, a mouse, a trackpad, a motion sensing camera, and other device configured to enable a user to interact with and manipulate data within the processing system 102.

Display 132 may be combined with processor 104, non-transitory memory 106, and/or user interface 130 in a shared enclosure, or may be peripheral display devices and may comprise a monitor, touchscreen, projector, or other display device known in the art, which may enable a user to view modality data, and/or interact with various data stored in non-transitory memory 106.

Next, FIG. 2 shows a UT health evaluation system 200, according to an embodiment. Indications of UT health based on patient data is processed via at least a trained machine learning model, which, in some aspects may be a trained clustering model 238, to provide more accurate and reliable UT health evaluation, as further discussed below.

UT health evaluation system 200 includes a computing device 212 for receiving patient data. The computing device 212 may be any suitable computing device, including a computer, laptop, mobile phone, etc. The computing device 212 includes one or more processors 224, one or more memories 226, and a user interface 220 for receiving user input and/or displaying information to a user.

In one implementation, the computing device 212 may be configured as a mobile device and may include an application 228, which represent machine executable instructions in the form of software, firmware, or a combination thereof. The components identified in the application 228 may be part of an operating system of the mobile device or may be an application developed to run using the operating system. In one example, application 228 may be a mobile application. The application 228 may also include web applications, which may mirror the mobile application, e.g., providing the same or similar content as the mobile application. In some implementations, the application 228 may be used to initiate patient data acquisition for UT health evaluation. The patient data may include patient response to one or more questionnaires. In some examples, additionally, patient data may include patient demographic data. In some embodiments, patient demographic data may be acquired via an electronic medical record (EMR) or an electronic health record (EHR) system. In still further examples, patient data may include patient medication data, and patient symptoms (based on the patient response to questionnaire) may be evaluated based on the patient medication data, for instance, to monitor disease progression and/or response to treatment.

Further, in some examples, the application 228 may be configured to monitor a quality of data acquired from each modality, and provide indications to a user regarding the quality of data. For example, during conditions when patient data includes audio data acquired via a microphone (e.g., audio data based on verbal response to questionnaire), if audio data quality acquired via the microphone is less than a threshold value (e.g., sound intensity is below a threshold, signal to noise ratio below a threshold, etc.), the application 228 may provide one or more indications to the user. For example, the one or more indications may include a voice and/or visual indication to adjust a position of the microphone.

The application 228 may be used for remote UT health evaluation as well as in-clinic UT health evaluation. In one example, the application 228 may include a clinician interface that allows an authenticated clinician to select a questionnaire from which data may be collected for UT health evaluation. The application 228 may allow the clinician to selectively store patient response data, initiate UT health evaluation, and/or view and store results of the UT health evaluation. In some implementations, the application 228 may include a patient interface and may assist a patient in acquiring patient data for UT health evaluation. As a non-limiting example, the patient interface may include options for activating a microphone 218 that is communicatively coupled to the computing device and/or integrated within the computing device.

In one example, memory 226 may include instructions that when executed causes the processor 224 to receive the patient data and further, pre-process the plurality of modality data. Pre-processing the patient data may include filtering patient data to remove noise (e.g., when audio response to questionnaire is acquired via the microphone 218). In some examples, patient data may be acquired via another device and transmitted to the computing device 212 for pre-processing. For example, patient response (e.g., language data or audio data) may be acquired via an input device, such as input device 125 at FIG. 1, and transmitted to the computing device 212 (e.g., via a wireless transceiver and/or a wired connection) for pre-processing and/or UT health evaluation.

In some examples, the patient data may be transmitted to UT health evaluation server 234 from the computing device 212 via a communication network 230, and the pre-processing step to remove noise may be performed at server 234. For example, the server 234 may be configured to receive the patient data from the computing device 212 via the network 230 and pre-process the patient data to reduce noise. The network 230 may be wired, wireless, or various combinations of wired and wireless.

In some examples, pre-processing may include determining one or more scores for a patient corresponding to one or more questionnaires. The one or more questionnaires may include one or more of Interstitial Cystitis Symptom and Problem Indices (ICSI/ICPI), Overactive Bladder Questionnaire (OABq), Genitourinary Pain Index (GUPI), and Pelvic Floor Disability Index (PFDI-20). Further, pre-processing may include determining sub-scores for each question in each questionnaire. For example, the patient may be presented with a set of answers for each question, and based on the answer, a sub-score may be determined. Further, a total score for each questionnaire may be determined. In some examples, only one questionnaire may be provided to the patient, and the UT health diagnosis may be performed based on patient response to the questionnaire. In some examples, more than one questionnaire may be provided to the patient and the UT health diagnosis may be performed based on patient response to more than one questionnaire.

In some embodiments, additionally or alternatively to the one or more questionnaires mentioned above, a UT health assessment questionnaire based on one or more diagnostic groups determined by the machine learning model may be utilized as input. As a non-limiting example, the UT health assessment questionnaire may be based on bladder pain syndrome, non-urologic urogenital pain, pelvic floor dysfunction, and urgency urinary incontinence. In some embodiments, the machine learning model may be utilized to identify one or more key features that contribute to a phenotype (example phenotypes include, but not limited to incontinence, bladder pain, persistency, urethral/vaginal pain, and bother). The UT health assessment questionnaire may then be based on the one or more key features that have a greater than threshold association with each phenotype.

The server 234 may include a UT health evaluation engine 236 for performing UT health condition analysis. In one example, the UT health evaluation engine 236 includes a trained machine learning model 237, such as a trained UT symptom classification model 238, for performing UT health evaluation. The UT symptom classification model 238 may be trained according to an unsupervised technique such as K-means clustering. For example, the unsupervised clustering technique may be used to categorize patient datasets into a number of diagnostic clusters (also referred to herein as diagnostic groupings or disease categories or disease clusters). The UT symptom classification model 238 may then be trained on the generated number of clusters, using a supervised learning technique, to classify patient data into a diagnostic cluster among the number of diagnostic clusters. In one example, a random forest model is trained on the clusters determined in some other way and incorporates the number of diagnostic clusters. As discussed above, the patient datasets are categorized into the different diagnostic clusters based on one or more of patient response data (e.g., symptoms indicated via one or more questionnaires regarding UT health) and patient demographic data, via an unsupervised learning algorithm. By applying unsupervised learning to the plurality of patient datasets, novel diagnostic categories are identified, which significantly improves accuracy in diagnosing a patient's urinary tract health condition. Experimental data showing improvement in accuracy of diagnosis is shown below under Example 1.

As one example, patient data, including response to the questionnaires and patient demographics are subjected to machine learning unsupervised clustering algorithms (k-means) to group the patients into groups based on similar patient phenotype. Further, an elbow method is applied to determine an optimal number of clusters. This method measures within group homogeneity and heterogeneity for different number of clusters, and the number of clusters is selected where the further addition of clusters demonstrates diminishing returns. By using an unsupervised algorithm, additional disease categories may be identified, which enables a clinician to provide appropriate treatment. As a result, patient response is improved. In particular, storage lower urinary tract symptoms (LUTS), including urinary urgency, frequency, nocturia, painful urination, and bladder discomfort are present with overlapping symptom manifestations, and therefore current approaches to clinical management and treatment of these conditions have been ineffective. By using an unsupervised machine learning algorithm that receives patient response data and demographic data as input, novel disease categories may be identified that enable suitable treatment regimen selection and therefore, facilitate effective disease management.

Further, in some embodiments, the trained machine learning model 237 further includes one or more trained classification and/or regression model(s) 240. The trained classification and/or regression models 240 may be a supervised learning model, such as a random forest model and a number of supervised learning models may be based on a number of clusters in the clustering model. Thus, if K clusters have been identified, K number of random forest models may be used. Thus, data in each cluster may be modelled via a random forest algorithm. When predicting new data, the category of new data may be first identified. For example, the category of new data may be determined via the UT symptom classification model. In some examples, the category of new data may be based on a distance between the new data and centroids of the different categories (that is, different clusters). The cluster to which the new data belongs may be determined based on the shortest distance to the centroid, for example. In some examples, upon identifying the cluster for the new data, the new data may be input into the corresponding supervised learning model for determining a severity of the disease condition represented by the new data. As mentioned above, the classification and/or regression model may be a supervised learning model, and thus may be trained according to learning techniques such as gradient descent algorithm, such that the classification and/or regression model 240 can be trained and can classify input data that were not used for training.

In some examples, the UT health evaluation engine may further include an electronic health record (EHR) processing logic for receiving patient information from an EHR system (not shown). The EHR system includes an EHR server and an EHR database storing patient health information. In some examples, the EHR system may further include an EHR interface server (not shown) for interfacing with the UT health evaluation server 234. In some examples, the UT health evaluation engine 236 may be integrated within the EHR system. The UT health evaluation engine 236 may receive patient data from the EHR, via network 230 or similar communication network (e.g., a wireless network, a wired network, or any combination of wireless and wired networks) between the UT health evaluation server and the EHR server, for example. In some examples, a clinician computing device (not shown) may be communicatively coupled to UT health evaluation server 150 via network 230 or another similar communication network (e.g., a wireless network, a wired network, or any combination of wireless and wired networks).

In one embodiment, an example system utilized to implement an UT health evaluation module may include a computing device that includes an interface, which may include a display. The computing device may be connected via a network to a server and a database. The computing device may include a memory and a transmitter for communicating wirelessly. The computing device and server may include a control system with one or more processors, for executing software-based instructions. This includes instructions for performing assessments, which may include displaying a series of questions from a patient questionnaire to a patient using the interface and receiving a patient's selection of answers through the interface.

The questions from the patient questionnaires may be displayed as text on a display of an interface. In other examples, the questions may be audibly spoken or read through a speaker associated with the computing device. Accordingly, a patient's answers may be input through a microphone on the computing device which would record a patient's verbally spoken answers.

Further, the computing device or database may store various machine learning algorithms and data sets. In some examples, the machine learning algorithms (e.g. k-means clustering model, random forest model) may be stored on the database and the patient's answers may be sent to the server over the network for processing (e.g. encrypted). In some examples the computing device may be a mobile device, a tablet, a computer or other suitable device. The interface 110 may be a touchscreen.

In some embodiments, the UT health evaluation engine may include a feature importance determination module that includes an feature importance determination algorithm, such as SHapely Additive Explanations (SHAP), Local Interpretable Model-agnostic Explanations (LIME), or any model-agnostic feature interpretation algorithm may be used on the supervised learning models to identify one or more features (e.g., urinary tract symptoms) that has a greater than threshold contribution to the diagnosis.

Methods

Figure 3A:
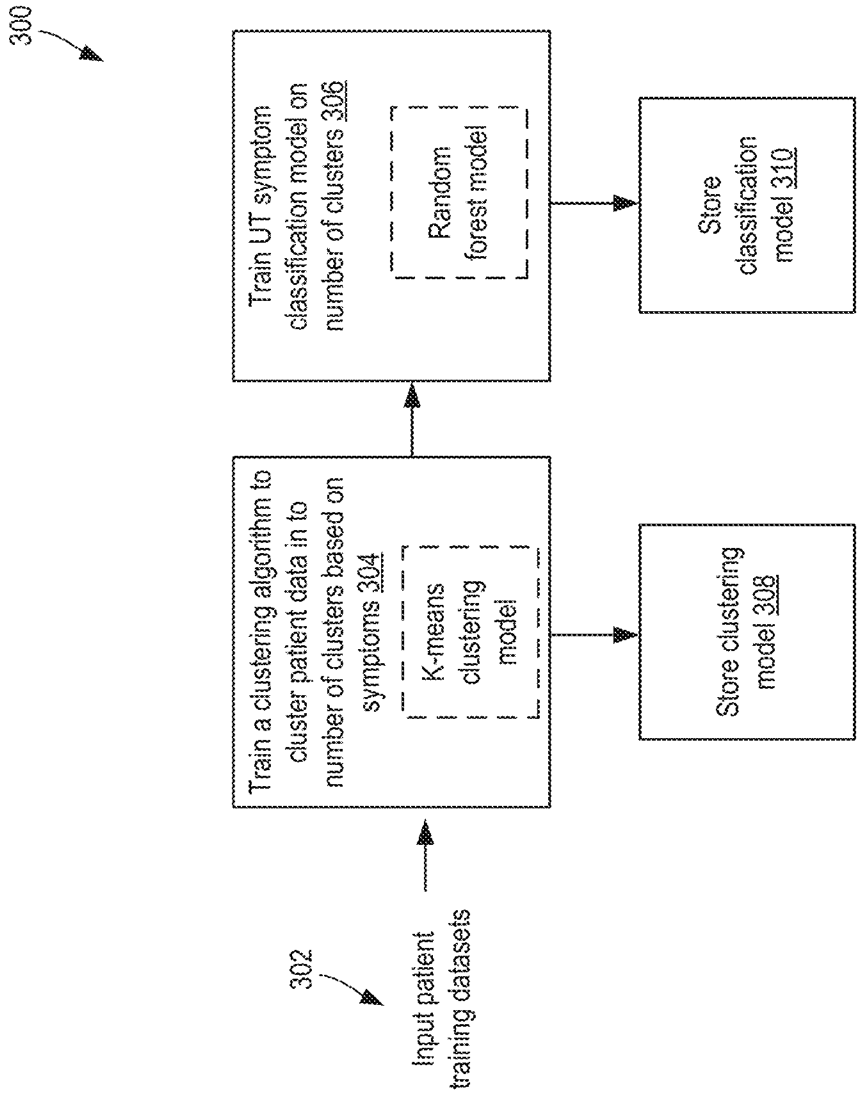
FIG. 3A shows a high level block diagram for training a machine learning model for urinary tract health evaluation, according to an embodiment of the disclosure.

FIG. 3A shows a block diagram illustrating an example method 300 for developing a machine learning model, such as the machine learning model 237 at FIG. 2, for UT symptom classification.

The machine learning model is trained using a plurality of patient datasets, where the plurality of datasets is unlabeled. The plurality of patient datasets is based on patient responses to one or more UT health questionnaires, including an Interstitial Cystitis Symptom and Problem Indices (ICSI/ICPI), Overactive Bladder Questionnaire (OABq), Genitourinary Pain Index (GUPI), and Pelvic Floor Disability Index (PFDI-20). In addition, patient demographic data may be included in the plurality of patient datasets.

In one example, the response to the questionnaires and patient demographics are input in to an unsupervised clustering algorithm (e.g., k-means) to group the patients into groups based on similar patient phenotype (304). The unsupervised algorithm is trained to determine an optimal number of clusters and the trained clustering model is stored (308). For example, an elbow method may be used to determine a K number of clusters. In one example, for lower urinary tract symptoms, a number of diagnostic clusters is five and include asymptomatic control cluster, bladder pain syndrome (BPS) cluster, non-urologic urogenital pain (NUPP) cluster, pelvic floor dysfunction cluster, and urgency urinary incontinence (UUI) cluster.

Figure 6:
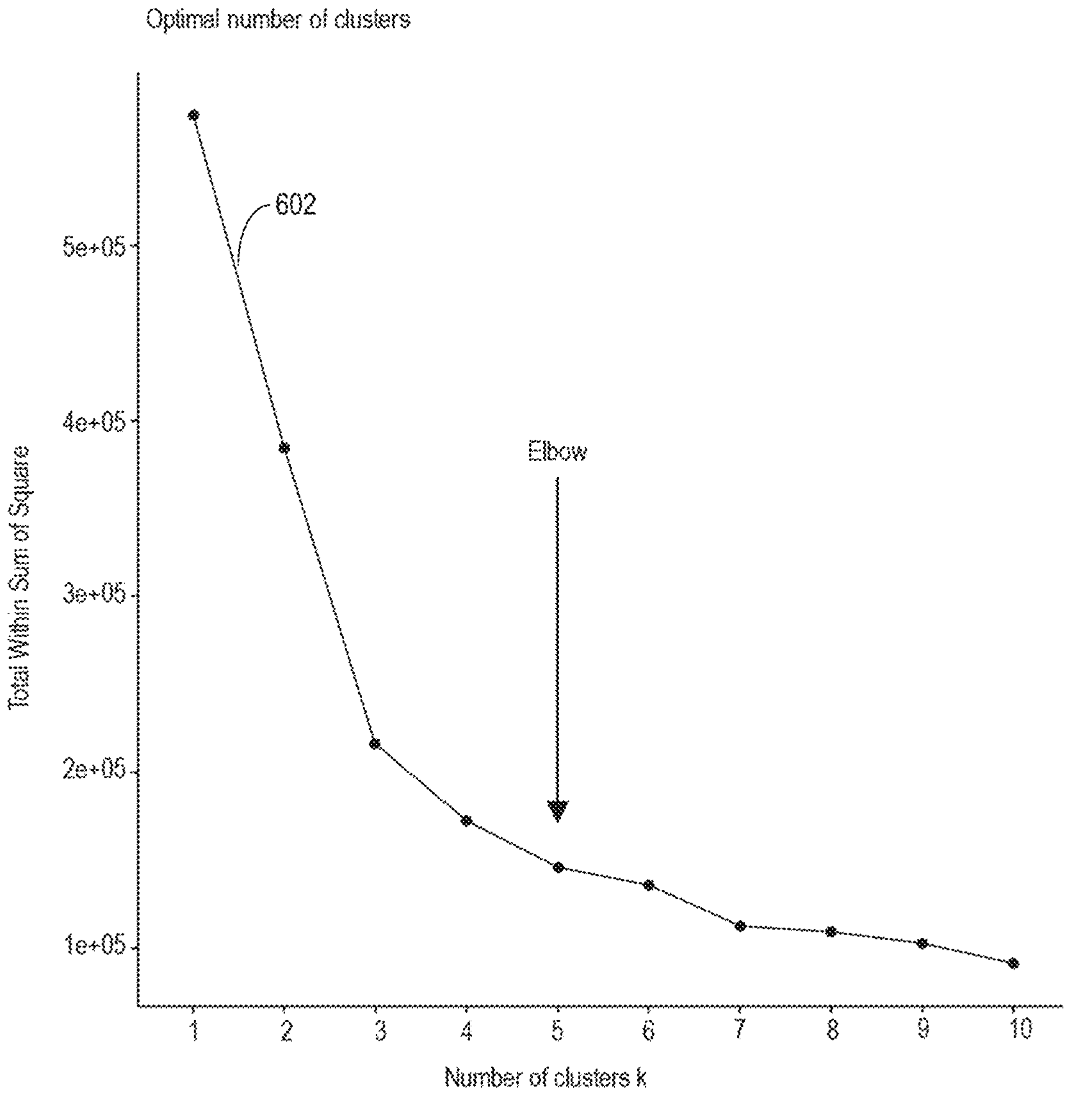
FIG. 6 shows a graph depicting example determination of an optimal number of clusters for the categorization of urinary tract symptoms.

In some examples, a graphical tool may be employed (e.g., elbow method) to estimate the optimal number of clusters, k, for a given task. If k increases, the distortion may decrease because the samples will be closer to the centroids they are assigned to. The elbow method may be used to identify the value of k where the distortion begins to increase most rapidly, as becomes clearer by plotting distortion for different values of k. This is illustrated, for example, in FIG. 6, where in order to determine what would be the optimal number of curve classes, the distortion is calculated for the range of cluster numbers from 1 to 10 and plotted as a graph for easy visualization (plot 602). The distortion is calculated as the average of the squared distances from the cluster centers of the respective clusters. In one example, the Euclidean distance metric is used. Other distance metrics, such as Mahalanobis distance and Manhattan distance may be used and are within the scope of the disclosure. The graph in FIG. 6 illustrates that after reaching 5-6 clusters, the distortion curve plateaus. Therefore, in this particular exemplary context for the data, an inference may be drawn that all the UT symptoms can be grouped into 5 different categories with a minimal impact on overall accuracy. In some examples, the number of clusters may be 6.

Next, at 306, a UT symptom classification model, such as UT symptom classification model 238, is trained on the number of clusters to output a diagnosis. In one example, the UT symptom classification model is a supervised learning model trained on the number of clusters generated by the clustering algorithm. As a non-limiting example, a random forest model is trained on a K number of clusters for identifying the diagnostic category. Thus, the trained UT symptom classification model is the random forest model trained on the K number of clusters. Thus, when new patient data is input, it is input into the random forest classifier (that is, the UT symptom classification model) and the output is one of the K number of diagnostic categories. Further, the trained classification model is stored.

Figure 3B:
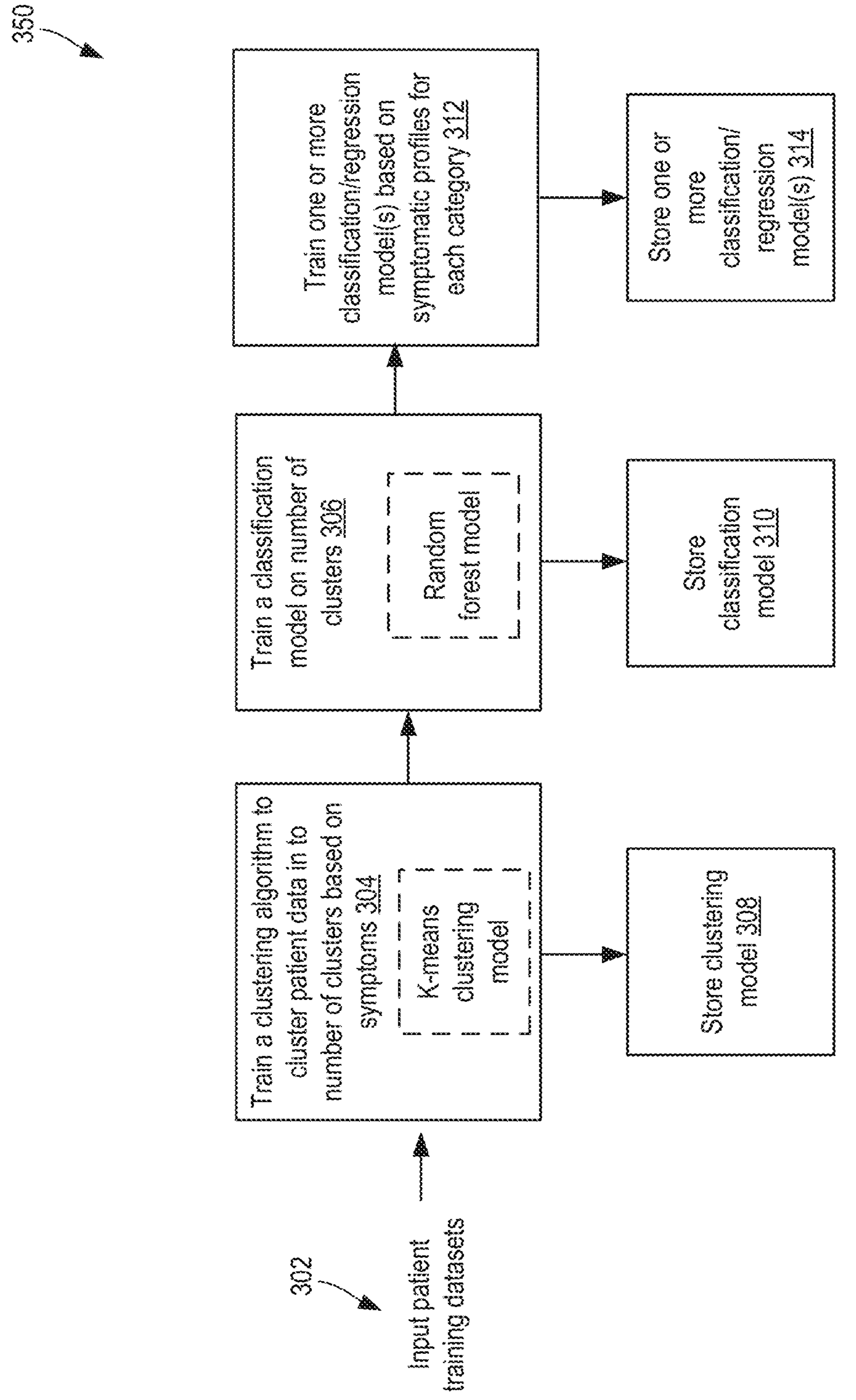
FIG. 3B shows a high level block diagram for training a machine learning model for urinary tract health evaluation, according to another embodiment of the disclosure.

In one example, as shown at FIG. 3B, one or more classification and/or regression models for each cluster may be generated (312). Referring now to FIG. 3B, it shows an example method 350 for training a machine learning model, such as the machine learning model 237 at FIG. 2, according to another embodiment of the disclosure. In one example, a classification model and/or a regression model may be generated for each diagnostic cluster.

In some aspects, the classification and/or regression models may be random forest models. In some embodiments, the classification and/or regression models may be used for evaluating the clusters. Accordingly, in one example, random forest models may be trained on both the clinician and machine generated cluster assignment (e.g., a first random forest model trained on machine generated clusters and a second random forest trained on clinician generated clusters) to assess the accuracy of each cluster assignment. For example, the random forest models may be generated from the data to predict the patient cluster (both the machine and clinician generated cluster groupings). In one example, data may be randomly partitioned into a training dataset (90%), and then the accuracy of the model may be assessed by generating predictions on the remaining 10% and comparing these predictions to the actual cluster assignments.

In another example, each cluster may be modelled using a classification model and/or a regression model for severity assessment. For example, each random forest model may be modelled based on each cluster, and may be trained to predict a severity of the disease condition. For example, the model which identifies different categories can be used to identify the unique symptomatic profiles for each category. From those profiles, indices for each category may be developed that provide a measure of severity. These are diagnostic measures of severity, generated by other models (such as a logistic regression, random forest, SVM, K-nearest neighbor, or Gaussian process classifiers etc.). Thus, the machine learning model may be used to identify the disease cluster to which the patient data belongs, and a corresponding second classifier (corresponding to the disease cluster identified) may be used to evaluate a measure of severity of the diagnosed disease. In this way, disease progression and response to treatment may be monitored using the trained machine learning model that includes the trained UT symptom classification model trained on the clusters generated by the unsupervised algorithm, and further includes one or more models for generating a classification output and/or a regression output for each disease category.

Thus, when multiple models are used for the severity analysis, in one example, a method for diagnosing UT tract symptoms may include determining a disease category (via a first machine learning model) for input patient data, selecting a model corresponding to the determined disease category, and determining a severity of the disease category (via a second machine learning model). In some examples, the second model that generates a severity level for each disease category may be a supervised learning model that is jointly trained (for the different diagnostic clusters) to receive patient data and output a severity level for the disease category identified by the first model.

In one example, the measure of severity may be one of a multi-level severity such as a low, medium, high, etc. In another example, the measure of severity may be based on a severity scale (e.g., a scale of 1-n, where n is ≥2), where each value corresponds to a degree of severity of the diagnosed urinary tract health condition. In yet another example, the measure of severity may be a severity score, the severity score based on one or more symptoms and severity of the one or more symptoms indicated by the patient in the one or more questionnaires.

In this way, a machine learning algorithm based on unsupervised learning and supervised learning is generated and used to effectively classify novel patient phenotypes.

Figure 4A:
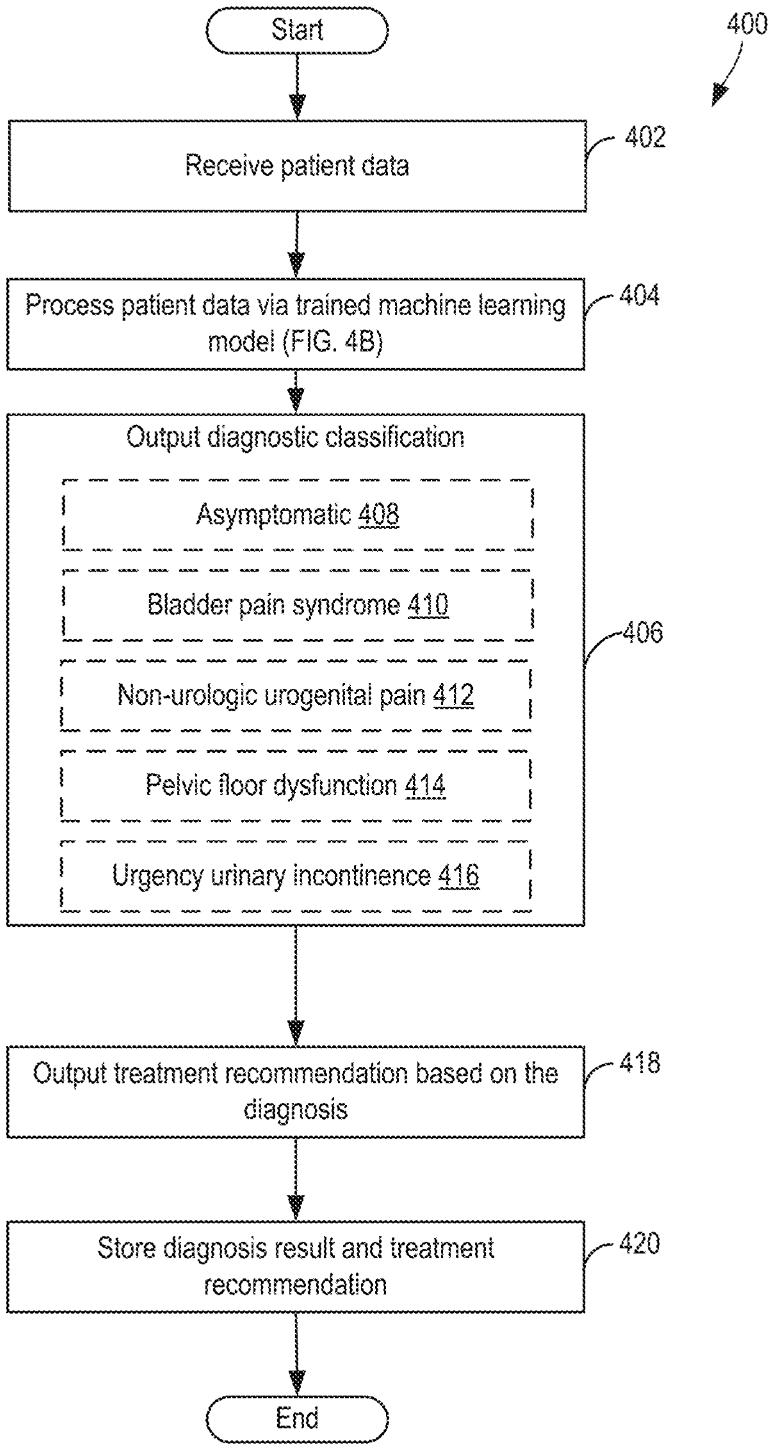
FIG. 4A shows a flow chart illustrating an example method for performing urinary tract health evaluation using a trained machine learning model, such as the machine learning model at FIG. 1 or FIG. 2, according to an embodiment of the disclosure.

FIG. 4A shows a high-level flow chart illustrating an example method 400 for administering and processing patient questionnaires using a computing device and providing a recommended diagnosis and/or treatment. The method 400 and other methods described herein may be executed by a processor, such as processor 224 or one or more processors of UT evaluation server 234 or a combination thereof. The processor executing the method 400 includes a trained machine learning model, such as model 237 at FIG. 2. As discussed above, the trained machine learning model may be trained to classify one or more UT disease condition, including but not limited to asymptomatic controls, bladder pain syndrome (BPS), non-urologic urogenital pain (NUPP), pelvic floor dysfunction, and urgency urinary incontinence (UUI), and/or output a regression result (e.g., severity of UT disease condition) pertaining to the one or more disease conditions.

At 402, the method 400 includes receiving patient data. For instance, in some examples, this includes displaying questions on an interface, such as input device 125 or computing device 212, from one or more patient questionnaires. In other examples, they may be read through a speaker or provided in other ways. Next, the method 400 includes receiving a patient's selection of answers through the interface. For instance, the patient may select a number category on the interface that relates to the severity of symptoms and/or discomfort the patient is feeling. The patient's answers, therefore may each be a quantitative assessment of symptoms that can be combined into a score.

At 404, the method 400 includes processing the answers using a trained machine learning model. In one example, the trained machine learning model may be a supervised learning model that is trained on a number of clusters generated by an unsupervised learning algorithm. In one example, the unsupervised learning model may be a clustering algorithm. In one example, the clustering algorithm may be a k-means clustering algorithm. As discussed above, the k-means clustering algorithm may be trained with training datasets comprising patient response data to questionnaires. Accordingly, the k-means clustering algorithm may be trained to categorize patient response data into diagnostic categories. As discussed below, in one example, a k-means classifier divided the training datasets into five categories: asymptomatic controls, bladder pain syndrome (BPS), non-urologic urogenital pain (NUPP), pelvic floor dysfunction, and urgency urinary incontinence (UUI). Further, a supervised classifier, such as a random forest classifier may be trained on the five categories to receive new patient response data from a patient and identify which diagnostic category the new patient data belongs to.

In another example, Ward's method may be used to generate a cluster dendrogram to obtain an estimation of number of clusters, an elbow method may be used to determine an optimal number of clusters, and then, the K-means algorithm may be used to categorize patient datasets.

In another example, other clustering algorithms, such as self-organizing maps may be used.

Further, in some examples, additionally, the trained machine learning model may include a trained classification and/or a trained regression model, for example to classify and/or regress a severity of the diagnosed disease condition. Accordingly, if there are K number of clusters, K number of trained classification models (and/or K number of trained regression models) may be modelled according to the data in each cluster.

In one example, the trained classification model and/or the trained regression model may be supervised learning models. In one example, the supervised learning models may be random forest classifiers. In other examples, other suitable models, such as support vector machine (SVM), K-nearest neighbor, or Gaussian process classifiers, may be utilized. In still further examples, convoluted neural network (CNN) models may be used.

Figure 4B:
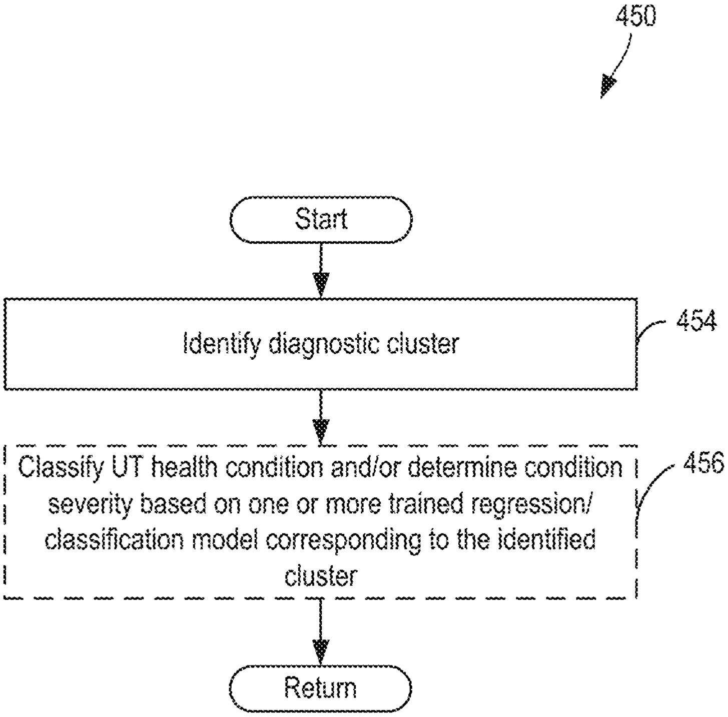
FIG. 4B shows a flow chart illustrating an example method for identifying and classifying patient data using the trained machine learning algorithm, according to an embodiment of the disclosure.

FIG. 4B shows a high-level flow chart illustrating an example method 450 for identifying and classifying patient data using the trained machine learning algorithm.

At 454, the method 450 includes identifying a diagnostic category based on the patient response data (that is, patient response to questionnaire). The diagnostic categories may be determined during training of the unsupervised learning algorithm. For storage lower urinary tract symptoms, the diagnostic categories include asymptomatic controls, BPS, NUPP, pelvic floor dysfunction, and UUI. Upon identifying the diagnostic category, in one example, the diagnosis may be output via a user interface.

In some examples, as indicated at 456, the patient data may be passed through a trained supervised learning model, such as a random forest model, to classify a level of severity of the identified disease category. In some examples, the random forest model may be used to identify one or more features in the patient data that contributed to the diagnosis.

Returning to FIG. 4A, after processing the patient data using the trained machine learning algorithm, the method 400 includes, at 406, outputting a diagnostic classification. In some examples, these diagnostic classifications could include: asymptomatic 408, bladder pain syndrome 410, non-urologic urogenital pain 412, pelvic floor dysfunction 414, and urgency urinary incontinence 416. As discussed above, these diagnostic categories may be formed using an unsupervised clustering algorithm (e.g. k-means clustering) to divide the data into groups using questionnaire and demographic data from a variety of patients.

Next, at 418, the method 400 includes recommending a treatment 240 based on the diagnostic classification. For instance, treatment comprises at least one of: pelvic floor physical therapy for pelvic floor dysfunction or gynecologic intervention for non-urologic pelvic pain. Following is a table of diagnostic categories and non-limiting examples of potential treatments that may be paired with them. The recommended treatments include but not limited to treatment with one or more of pharmaceutical compositions (e.g., pharmaceutical composition including examples indicated in the table below), nerve stimulation therapies, physical therapies, and neuromodulation therapies.

TABLE 2

Diagnostic categories and potential treatments

| Diagnostic Category | Recommended Treatment(s) |
|---|---|
| Bladder Pain Syndrome | Intravesical instillations, pentosan polysulfate, amitriptyline, bladder analgesics (e.g. phenazopyridine) |
| Non-urologic urogenital pain | gynecologic intervention, topical anesthetics (e.g. lidocaine), topical neuromodulatory agents (e.g. gabapentin) |
| Pelvic floor dysfunction | pelvic floor physical therapy, trigger point injections, muscle relaxants (systemic or local), pelvic floor biofeedback |
| Urgency urinary incontinence | Antimuscarinic and sympathomimetic oral medications (e.g. oxybutynin, tolterodine, mirabegron), intradetrusor onabotulinum toxin, sacral neuromodulation, posterior tibial nerve stimulation |

Next, the method 400 includes storing one or more of the generated diagnosis, the treatment options, and a severity of the disease condition. In some examples, the treatment recommendation may be based on the diagnosis category and a severity of the diagnosed disease category.

In some examples, the method further includes prescribing the treatment to a patient. In one example, prescribing the treatment to a patient includes updating an electronic health record of the patient. In some examples, additionally, an indication, which in some aspects may be an automatic indication or initiated by a health care provider, may be delivered to the patient regarding the prescribed treatment, via a health care app etc.

Patient Treatment

In one representation, a method for treating or ameliorating one or more urinary tract (UT) symptoms in a subject in need comprises: determining a diagnosis of a UT health condition using a trained machine learning algorithm receiving patient response data as input, the patient response data including patient indicated responses to one or more UT health questionnaires; optionally, determining, a severity of the diagnosed UT health condition using a second machine learning model, the second machine learning model trained to output the severity level; determining a treatment regimen based on the diagnosis; and treating the patient according to the treatment regimen. In a first example of the method, the trained machine learning algorithm is trained on patient datasets labelled according to a plurality of diagnostic clusters generated by an unsupervised learning algorithm. In a second example of the method, which optionally includes the first example, the trained machine learning algorithm is selected from the group consisting of random forest algorithm, support vector machine, k-nearest neighbor, Gaussian process classifier, and convolutional neural network. In a third example of the method, which optionally includes one or more of the first and the second examples, the plurality of diagnostic clusters comprises asymptomatic controls, bladder pain syndrome (BPS), non-urologic urogenital pain (NUPP), pelvic floor dysfunction, and urgency urinary incontinence (UUI). In a fourth example of the method, which optionally includes one or more of the first through third examples, the one or more questionnaires includes one or more of Interstitial Cystitis Symptom and Problem Indices (ICSI/ICPI), Overactive Bladder Questionnaire (OABq), Genitourinary Pain Index (GUPI), and Pelvic Floor Disability Index (PFDI-20).

In another representation, a method for a UT tract health condition comprises: evaluating a UT health condition of a patient using a trained machine learning algorithm receiving patient response data as input, the patient response data including patient indicated responses to one or more UT health questionnaires; optionally, determining, a severity of the diagnosed UT health condition using a second machine learning model, the second machine learning model trained to output the severity level; determining a treatment regimen based on the diagnosis; and treating the patient according to the treatment regimen. In a first example of the method, the trained machine learning algorithm is trained on patient datasets labelled according to a plurality of diagnostic clusters generated by an unsupervised learning algorithm. In a second example of the method, which optionally includes the first example, the trained machine learning algorithm is selected from the group consisting of random forest algorithm, support vector machine, k-nearest neighbor, Gaussian process classifier, and convolutional neural network. In a third example of the method, which optionally includes one or more of the first and the second examples, the plurality of diagnostic clusters comprises asymptomatic controls, bladder pain syndrome (BPS), non-urologic urogenital pain (NUPP), pelvic floor dysfunction, and urgency urinary incontinence (UUI). In a fourth example of the method, which optionally includes one or more of the first through third examples, the one or more questionnaires includes one or more of Interstitial Cystitis Symptom and Problem Indices (ICSI/ICPI), Overactive Bladder Questionnaire (OABq), Genitourinary Pain Index (GUPI), and Pelvic Floor Disability Index (PFDI-20).

In some examples, a health care provider may treat the patient based on the recommended treatment. Treating the patient based on the recommended treatment includes administering the treatment to the patient. As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

Furthermore, in some examples, the system may reapply the assessments to the patient after the treatments, to record and assess the effectiveness of the treatments. Accordingly, the system could then learn what treatments are most effective based on the patients answers to patient questionnaires and their demographic data. Example treatments are shown in table 2.

EMBODIMENTS

Embodiment 1. A system for evaluating a patient, the system comprising: a display device; a user interface; a memory; and a control system coupled to the memory and comprising one or more processors, the control system configured to execute a machine executable code stored thereon to cause the control system to: display, on the display device, a series of questions from a set of urinary health questionnaires comprising text and answers for each question; receive, from the user interface, a selection of answers from a patient of each of the displayed series of questions; and process, using a trained machine learning model, the received selection of answers to output a classification of the patient's urinary tract symptoms; wherein the trained machine learning model is a supervised learning model trained based on a plurality of diagnostic clusters generated by an unsupervised learning model.

Embodiment 2. The system of embodiment 1, wherein the classification of the patient's urinary tract symptoms comprises one of asymptomatic controls, bladder pain syndrome, non-urologic urogenital pain, pelvic floor dysfunction, or urgency urinary incontinence.

Embodiment 3. The system of one or more of embodiments 1 and 2, further comprising determining a recommended treatment based on the classification, and outputting the recommended treatment.

Embodiment 4. The system of one or more of embodiments 1-3, wherein the trained machine learning model is trained using a training dataset, the training dataset comprising a plurality of patient response datasets, the plurality of patient response datasets including patient response to the urinary tract health questionnaires from a plurality of patients.

Embodiment 5. The system of one or more of embodiments 1-4, wherein processing using the trained machine learning model comprises classifying the patient response into a diagnostic cluster from a plurality of diagnostic clusters into which a plurality of patient response datasets of a training dataset has been clustered.

Embodiment 6. The system of one or more of embodiments 1-5, wherein the machine learning model is trained based on one or more of a k-means clustering algorithm and an elbow method to determine a number of the plurality of clusters.

Embodiment 7. The system of one or more of embodiments 1-5, wherein the machine learning model is trained based on one or more of a Ward's method of hierarchical clustering, an elbow method to determine a number of clusters, and a k-means clustering algorithm.

Embodiment 8. The system of one or more of embodiments 1-7, wherein the trained machine learning model further comprises, for each cluster, a classification model and/or a regression model.

Embodiment 9. The system of one or more of embodiments 1-8, wherein the classification and/or the regression models are random forest models.

Embodiment 10. The system of one or more of embodiments 1-9, wherein the control system is further configured to predicting an effectiveness of a prospective treatment based on the classification.

Embodiment 11. The system of embodiment one or more of embodiments 1-10, wherein the set of patient questionnaires comprises one or more of Interstitial Cystitis Symptom and Problem Indices (ICSI/ICPI), Overactive Bladder Questionnaire (OABq), Genitourinary Pain Index (GUPI), and Pelvic Floor Disability Index (PFDI-20).

Embodiment 12. The system of one or more of embodiments 1-11, wherein the supervised learning model is a random forest model; and wherein the random forest model is trained using a dataset labelled using an unsupervised k-means clustering process on data from the set of patient questionnaires.

Embodiment 13. The system of one or more of embodiments 1-12, wherein the control system is further configured to:

store the trained machine learning model in the memory;

process the trained machine learning model with a second set of patient questionnaire and demographic data to output an updated random forest model; and store the updated machine learning model in the memory.

Embodiment 14. The system of one or more of embodiments 1-13, wherein process, using the trained machine learning model, the received selection of answers to output the classification of the patient's urinary tract symptoms, further comprises process a set of demographic data describing the patient.

Embodiment 15. A method for diagnosing a urinary tract health condition, the method comprising: receiving, via a user interface, patient response data for a patient, the patient response data corresponding to one or more symptoms of urinary tract and/or severity of symptoms of urinary tract; processing the received patient response data using a trained machine learning model to output a diagnosis of the patient's urinary tract symptoms; and outputting a recommendation for treatment based on the classification of the patient's urinary tract symptoms; wherein the trained machine learning model is trained according to dataset labelled using a plurality of diagnostic clusters generated by an unsupervised learning algorithm.

Embodiment 16. The method of embodiment 15, further comprising, generating a measure of severity of the patient's urinary tract symptoms using a second machine learning model based on the classification of the patient's urinary tract symptoms.

Embodiment 17. The method of one or more of embodiments 15-16, wherein the unsupervised learning algorithm is a k-means clustering algorithm; wherein a number of the plurality of diagnostic clusters is determined according to an elbow method; and wherein the trained machine learning algorithm is a random forest algorithm.

Embodiment 18. The method of one or more of embodiments 1-17, wherein the second machine learning model is a supervised learning model that is trained to output the measure of severity for each diagnosis determined by the trained machine learning model.

Embodiment 19. The method of one or more of embodiments 1-18, wherein the classification of the patient's urinary tract symptoms comprises one of asymptomatic controls, bladder pain syndrome, non-urologic urogenital pain, pelvic floor dysfunction, or urgency urinary incontinence.

Embodiment 20. The method of one or more of embodiments 1-19, wherein the patient response data is based on patient responses to one or more patient questionnaires, the one or more patient questionnaires comprising one or more of Interstitial Cystitis Symptom and Problem Indices (ICSI/ICPI), Overactive Bladder Questionnaire (OABq), Genitourinary Pain Index (GUPI), and Pelvic Floor Disability Index (PFDI-20).

Embodiment 21. A system for evaluating a patient, the system comprising: an device including a user interface; a memory; a control system comprising one or more processors coupled to the memory, the memory storing executable code and a trained machine learning model, the control system configured to execute the machine executable code to cause the control system to: receive, via the user interface, a set of patient data, the set of patient data including one or more urinary tract symptom data of the patient; and process, using a trained machine learning model, the received set of patient data to output a urinary tract health diagnosis based on the one or more urinary tract symptom data; wherein the trained machine learning model is trained to assign the set of patient data to a disease cluster among a plurality of disease clusters and output the urinary tract health diagnosis.

Embodiment 22. The system of embodiment 21, wherein the trained machine learning model is further trained to classify the set of patient data based on a supervised learning model, the supervised learning model trained to classify a severity level of the urinary tract health diagnosis determined based on the disease cluster.

Embodiment 23. The system of one or more of embodiments 21-22, wherein the urinary tract health diagnosis comprises at least one of: asymptomatic controls, bladder pain syndrome, non-urologic urogenital pain, pelvic floor dysfunction, or urgency urinary incontinence.

Embodiment 24. The system of one or more of embodiments 21-23, wherein the control system is further configured to determine a recommended treatment based on the classification, and output the recommended treatment via the user interface.

Embodiment 25. The system of one or more of embodiments 21-24, wherein the plurality of clusters is generated based on an unsupervised learning model.

Embodiment 26. The system of one or more of embodiments 21-25, wherein the unsupervised learning model is trained based on one or more of a k-means clustering algorithm and an elbow method to determine a number of the plurality of clusters.

Embodiment 27. The system of one or more of embodiments 21-26, wherein the trained machine learning algorithm further comprises, for each of the plurality of disease clusters, a classification model and/or a regression model.

Embodiment 28. The system of one or more of embodiments 21-27, wherein the classification and/or the regression models are random forest models.

Embodiment 29. The system of one or more of embodiments 21-28, wherein the set of patient data is based on a series of questions from a set of urinary health questionnaires comprising text and answers for each question and a selection of answers from the patient of each of the series of questions; and wherein the set of patient questionnaires comprises one or more of Interstitial Cystitis Symptom and Problem Indices (ICSI/ICPI), Overactive Bladder Questionnaire (OABq), Genitourinary Pain Index (GUPI), and Pelvic Floor Disability Index (PFDI-20).

EXAMPLES

The following examples are provided to better illustrate the claimed invention and are not intended to be interpreted as limiting the scope of the invention. To the extent that specific materials or steps are mentioned, it is merely for purposes of illustration and is not intended to limit the invention. One skilled in the art may develop equivalent means or reactants without the exercise of inventive capacity and without departing from the scope of the invention.

Example 1: Experimental Data

In one example, the disclosed technology was utilized to cluster patients into diagnostic categories based on their responses to patient questionnaires and demographic data using a k-means clustering algorithm. The algorithm separated the common diagnosis of interstitial cystitis and overactive bladder into four, more specific symptom clusters of urgency incontinence, bladder pain syndrome, pelvic floor dysfunction, and non-urologic pelvic pain.

The following set of experimental data is provided to better illustrate the claimed invention and is not intended to be interpreted as limiting the scope.

Storage lower urinary tract symptoms (LUTS), including urinary urgency, frequency, nocturia, painful urination, and bladder discomfort, contributes to a heavy burden of illness and are classically categorized into conditions with sizable symptomatic overlap. As no objective diagnostic criteria exists to differentiate these conditions, we aimed to apply machine learning algorithms to generate and validate novel diagnostic phenotypes of patients with storage LUTS.

Lower urinary tract symptoms (LUTS) form a set of complex and poorly understood symptoms that encompass problems with normal holding of urine (storage) and bladder emptying (voiding). The storage subset of LUTS, including urinary urgency, frequency, nocturia, painful urination, and bladder discomfort, contributes to a heavy burden of illness and are categorized into several conditions with sizable symptomatic overlap (e.g. interstitial cystitis/painful bladder syndrome (IC/BPS) and overactive bladder (OAB))(1). These disorders are frequently chronic and debilitating, and negatively impact a patient's quality of life (2). Further, these disorders represent a significant economic burden, with an estimate annual cost to the health care system in excess of 80 billion dollars per year (3). Compounding this is the fact that appropriate diagnosis and treatment is hampered by the challenges in identifying and classifying these condition (4).

Two syndromes, IC/BPS and OAB, present particular diagnostic challenges as there are currently no definitive tests or markers available. Diagnosis is thus based on subjective patients reported symptoms (5,6). IC/BPS is by bladder pain while the key symptom of OAB is urinary urgency (5). Although these two conditions are classically considered distinct entities, recent evidence suggests there is actually significant symptomatic overlap between them (7).

Machine learning represents a new body of analytical methods that have shown promise in assisting the clinician in the diagnosis of disease in several fields (8-13).

Given the known clinical dilemmas in diagnosing storage LUTS, with no objective diagnostic criteria exists to differentiate these conditions, we aimed to apply machine learning algorithms to generate diagnostic groupings based on readily available clinical data and to further validate these novel diagnostic groupings.

Methods:

With IRB approval and patient consent, 514 consecutive patients presenting to a tertiary referral center's Urogynecology specialty clinic between June and December 2017 completed the Interstitial Cystitis Symptom and Problem Indices (ICSI/ICPI), Overactive Bladder Questionnaire (OABq), Genitourinary Pain Index (GUPI), and Pelvic Floor Disability Index (PFDI-20). The patients completed the surveys regardless of referring diagnosis, so patients with non-pelvic floor disorders chief complaints were included (ie microhematuria). These patients were assigned a clinical diagnosis (overactive bladder, interstitial cystitis/bladder pain syndrome, pelvic floor dysfunction and all others) by two FPMRS specialists in a manner independent and blinded from the other physician's diagnosis and the results of the clustering algorithm (clinician cluster groups).

The response to the questionnaires and patient demographics were subjected to machine learning unsupervised clustering algorithms (k-means) to group the patients into groups based on similar patient phenotype. The R stats package kmeans function was applied. The elbow method was applied to determine the optimal number of clusters. This method measures within group homogeneity and heterogeneity for different number of clusters, and the number of clusters is selected where the further addition of clusters demonstrates diminishing returns.

The mean scores for patient characteristics (Age, Height and Weight) and well as each survey response were calculated. ANOVA testing was applied to assess for significant differences in the intragroup means for each of these variables between the different cluster groups (ie differences between the individual groups for each cluster groups were assessed). The 5 groups created would ultimately be referred to as the machine cluster groups 1-5.

Random forest models were then created and trained on both the clinician and machine generated cluster assignment with the randomForest package in R to assess the accuracy of each cluster assignment. The random forest models were created from the data to predict the patient cluster (both the machine and clinician generated cluster groupings). The Carat package in R was used to assess the accuracy of these models with 10-fold cross validation. This methodology randomly partitions 90% of the data into a training dataset, and then assess the accuracy of the model by generating predictions on the remaining 10% and comparing these predictions to the actual cluster assignments. The accuracy of the predictions was reported (the overall proportion of correct predictions) as was the kappa statistic (adjusted accuracy accounting for likelihood of a correct prediction by chance alone, range 0-1). Kappa is commonly interpreted as Very Good (0.8-1.0), Good (0.60-0.80), Moderate (0.40-0.60), Fair (0.2-0.40) and Poor (less than 0.20). All analysis was performed in R version 3.6.1.

Results:

514 consecutive patients completed the surveys between June and December 2017. Overall, the patients were of a mean age of 58.7 years. A total of 95, 275, 76 and 68 patients were assigned the diagnosis of Other/non-pelvic floor disorder (clinician cluster 1), overactive bladder (clinician cluster 2), interstitial cystitis (clinician cluster 3) and pelvic floor dysfunction (clinician cluster 4), respectively, by the FPMRS specialist physicians (Table 1, FIG. 1). Patients in the clinician clusters 3 and 4 were of younger age and lower weight. Clinician cluster group 1 had overall lower questionnaire responses, most consistent with controls. Clinician cluster group 2 had lower responses to many of the questionnaire components with the exceptions of the OABq5, 6 and 8 as well as the GUPI9, PFD20_15, 16 and 17 components (incontinence and frequency). Thus, this group was consistent with patient with the overactive bladder phenotype. The clinician cluster group 3 had higher responses to the ICPI4, OABq2, q3, q5 and q8 as well as GUPI2C, 2D, 2C, 3, 4, 5 and 6. These questions broadly encompassed painful bladder filling and symptoms of overactive bladder. Clinician cluster group 4 had similarly higher responses to the same components at the third group, but with high scores in the PFD_5, 12, 13, 14, 16, 18 and 19 components (GI distress components) (Table 1).

Figure 5A:
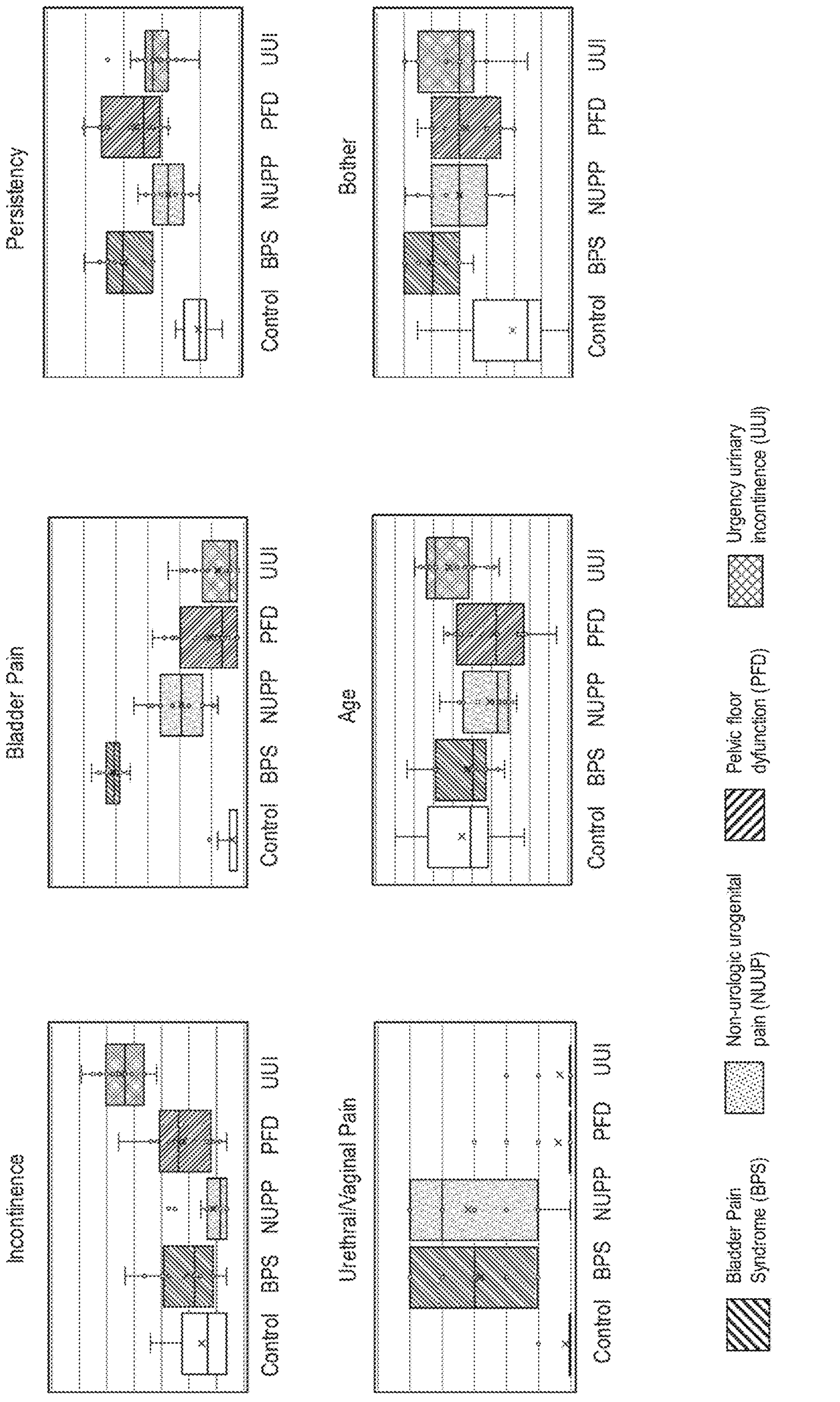
FIG. 5A shows a graph illustrating feature distribution among a set of machine learning diagnostic clusters generated based on a trained machine learning algorithm for lower urinary tract symptoms.
Figure 7:
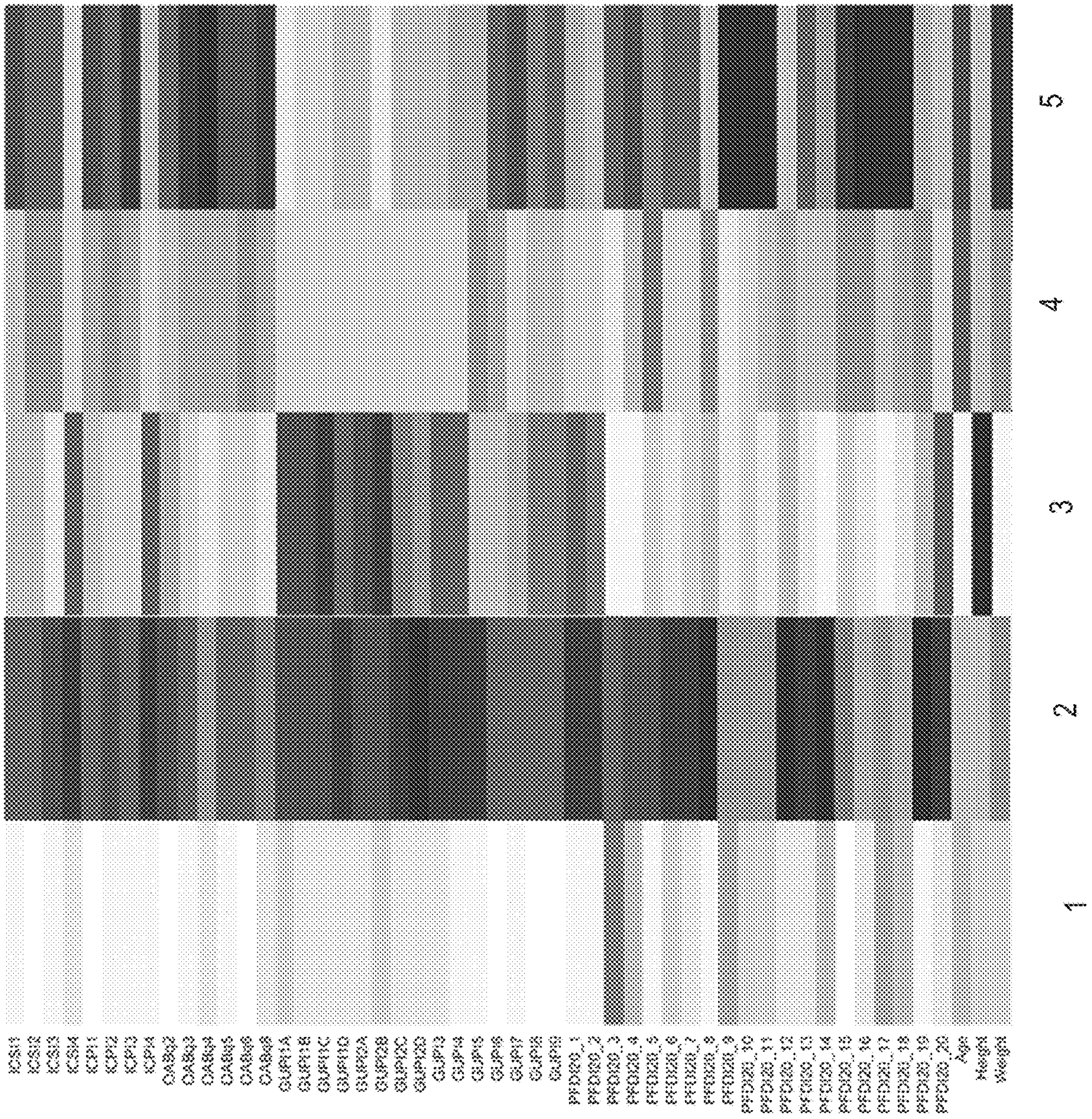
FIG. 7 shows an example of a heat map of survey responses and patient characteristics for each of the machine learning generated clusters.

By the elbow method, the optimal number of clusters for the k-means algorithm was determined to be 5 (FIG. 6). Application of the k-means algorithm generated 5 groups with a total of 142, 85, 111, 121 and 55 patients in each group. After assessment of the predominant characteristics of each cluster (Table 1, FIGS. 5A, 5B, and 7), these clusters were defined as other/non-pelvic floor disorders (machine cluster 1), bladder pain syndrome (machine cluster 2), non-urologic urogenital pain (machine cluster 3), pelvic floor dysfunction (machine cluster 4) and urgency urinary incontinence (machine cluster 5). Patients in the Cluster groups 4 and 5 were older than the other groups. FIG. 5B shows a table 500 depicting machine learning generated diagnostic clusters, their corresponding diagnostic classification (that is, diagnosis of each cluster), and their salient features. Cluster 1 patients had overall low questionnaire responses for all components, most consistent with the asymptomatic controls. Cluster 2 patients had high responses to most of the questionnaire components, most consistent with bladder pain syndrome/interstitial cystitis. The third clusters highest responses were related to vaginal and urethral pain, most consistent with non-urologic pelvic pain. The fourth clusters highest responses centered around the components PFD20q5, the GUPI Urinary Scores and the GUPIq3. We defined the summation of these components as Persistency and this was the hallmark characteristic of the fourth machine cluster group. Finally, the machine cluster groups 5 response were highest in the overactive bladder and incontinence specific components, most consistent with patients suffering from urge urinary incontinence (Table 1, FIGS. 5A, 5B, and 7).

The random forest modeling for prediction of a patient's clinician and machine diagnostic groups revealed that the diagnostic accuracy was higher (accuracy 89.8%, Kappa 0.869-Very good) for the machine generated cluster assignment as compared to the cluster generated by the clinicians (accuracy 79.0%, Kappa 0.641-Good) for specialist physician diagnosis.

Discussion

Machine learning algorithms were successfully applied to classify patients with storage LUTS symptoms into five logical phenotypic-specific groups based on validated patient-reported outcomes. The clusters were interpreted as non-pelvic floor disorders, bladder pain syndrome, non-urologic urogenital pain, pelvic floor dysfunction and urgency urinary incontinence. Validation of these diagnostic clusters revealed high reproducibility and an accuracy of nearly 90%. Further, the machine learning generated clusters more accurately classified these patients than the clinical classification by sub-specialist Urologists.

The findings here are novel and timely given the significant burden these conditions place on patients and the healthcare system. The first step in improving the care delivered to these patients is improving the diagnosis and classification of patients with storage LUTS, which is known to be notoriously difficult to correctly classify (21). Despite the wide prevalence of these conditions, little progress has been made in improving the current diagnostic schema.

The machine generated clusters distinctly differentiate those patients who suffer from and IC/BPS clinical picture from those suffering from OAB. Although differentiating these patients may seem straightforward, obtaining a correct diagnosis is complicated by significant symptomatic overlap. Prior work by our group studied the clinical overlap between of urinary tract symptoms between OAB and IC/BPS. In one study it was noted that there was a significant proportion of patients carrying an OAB diagnosis who suffered from significant bladder pain (35%) and urge incontinence was present in 35% of patients with IC/BPS. A nomogram which included combining responses from the OAB-q, IC SI, ICPI and female Genitourinary Pain Index (fGUPI) questionnaires for patients with IC/BPS and OAB resulted in a diagnostic accuracy of 94% (22). Additionally, findings from the first phase of The Multidisciplinary Approach to the Study of Chronic Pelvic Pain (MAPP) Research Network which consisted of 424 participants from multiple sites determined that Urologic chronic pelvic pain syndrome (UCPPS) and urinary symptoms (urgency and/or frequency) have different clinical histories and should be assessed separately (21).

The machine generated clusters also identify two other groups that could be confused with true IC/BPS or OAB in clinical scenarios: non-urologic urogenital pain and pelvic floor dysfunction. Non-urologic pelvic pain has been suggested to exist in up to 34% of patients diagnosed with OAB (23). However, this type of pelvic pain is not always accompanied by definite urologic symptoms but is nevertheless frequently confused with true IC/BPS. For example, one type of non-urologic pelvic pain is vulvodynia, which has been estimated to exist in 10-16% of the female population (24). Other possibilities include etiologies such as endometriosis, adenomyosis, or pelvic inflammatory disease (24). Further study is warranted to further assess the specific locations and etiology of women in this cluster. Similarly, pelvic floor dysfunction or Myofascial pain associated with myofascial trigger points can be mistaken for IC/BPS or OAB (25). These conditions (non-urologic urogenital pain and pelvic floor dysfunction) are less frequently recognized and their misclassification can result in the incorrect treatment being recommended which leads to patient and clinician frustration. If the correct diagnosis is made however, the correct treatment can be recommended (i.e. pelvic floor physical therapy for pelvic floor dysfunction or gynecologic intervention for non-urologic pelvic pain).

Our study involved a large number of patients (over 500) who were consecutively included (regardless of referral diagnosis). This means that our cohort not only included a control group, but moreover is likely representative of the true patient population referred to urogynecologic practice. Furthermore, this algorithm relies only on validated questionnaire responses, and thus can be assigned without assessment by a subspecialized physician. Thus, this novel LUTS classification algorithm can potentially be utilized to assign treatment plans without the need for sub-specialist evaluation, to which access can be limited.

TABLE 1

Patient characteristics and survey scores by clinical and machine learning diagnostic clusters

| | Clinical Diagnosis Groups | | | | Machine learning (ML) Diagnosis Groups | | | | |
|---|---|---|---|---|---|---|---|---|---|
| Variable | 1 (n = 95) | 2 (n = 275) | 3 (n = 76) | 4 (n = 68) | 1 (n = 142) | 2 (n = 85) | 3 (n = 111) | 4 (n = 121) | 5 (n = 55) |
| Age* | 52.29 | 67.13 | 46.96 | 46.92, p < 0.001 | 57.06 | 57.05 | 53.52 | 63.68 | 65.08, p < 0.001 |
| Weight | 150.77 | 160.19 | 140.51 | 146.16, p = 0.002 | 150.23 | 156.12 | 146.59 | 157.03 | 165.77, p = 0.003 |
| Height | 63.72 | 63.89 | 64.52 | 64.38, p = 0.050 | 63.75 | 63.79 | 64.88 | 63.08 | 63.81, p = 0.579 |
| ICSI1 | 0.81 | 1.92 | 2.34 | 1.51, p < 0.001 | 0.38 | 3.06 | 1.50 | 1.73 | 3.53, p < 0.001 |
| ICSI2 | 1.81 | 2.80 | 3.54 | 2.93, p < 0.001 | 1.16 | 3.95 | 2.74 | 3.14 | 4.14, p < 0.001 |
| ICSI3 | 1.25 | 1.97 | 2.08 | 1.63, p = 0.300 | 1.12 | 2.71 | 1.29 | 2.08 | 2.63, p < 0.001 |
| ICSI4 | 0.36 | 0.92 | 2.81 | 1.11, p < 0.001 | 0.27 | 2.68 | 2.01 | 0.48 | 0.51, p = 0.433 |
| ICPI1 | 1.08 | 2.13 | 2.56 | 2.28, p < 0.001 | 0.56 | 3.24 | 1.98 | 2.30 | 3.37, p < 0.001 |
| ICPI2 | 0.87 | 2.03 | 2.14 | 1.86, p < 0.001 | 0.70 | 3.06 | 1.37 | 2.13 | 2.96, p < 0.001 |
| ICPI3 | 0.67 | 1.71 | 1.67 | 1.38, p = 0.049 | 0.29 | 2.61 | 1.01 | 1.59 | 3.40, p < 0.001 |
| ICPI4 | 0.40 | 1.37 | 3.29 | 1.93, p < 0.001 | 0.27 | 3.38 | 2.71 | 0.75 | 1.42, p = 0.048 |
| OABq2 | 1.74 | 3.17 | 3.97 | 3.63, p < 0.001 | 1.45 | 4.69 | 3.19 | 3.08 | 4.62, p < 0.001 |
| OABq3 | 1.74 | 2.90 | 2.82 | 2.61, p = 0.036 | 1.28 | 3.98 | 2.04 | 2.79 | 4.90, p < 0.001 |
| OABq4 | 2.24 | 2.71 | 1.84 | 2.33, p = 0.260 | 1.73 | 2.96 | 1.59 | 2.78 | 4.48, p < 0.001 |
| OABq5 | 2.02 | 3.31 | 3.18 | 2.85, p = 0.086 | 1.76 | 4.30 | 2.41 | 3.34 | 4.57, p < 0.001 |
| OABq6 | 2.11 | 3.44 | 3.47 | 3.44, p < 0.001 | 1.81 | 4.42 | 2.64 | 3.84 | 4.58, p < 0.001 |
| OABq8 | 1.64 | 2.59 | 1.89 | 2.23, p = 0.582 | 1.25 | 3.25 | 1.28 | 2.66 | 4.26, p < 0.001 |
| GUPI1A | 0.09 | 0.23 | 0.49 | 0.37, p < 0.001 | 0.09 | 0.53 | 0.54 | 0.10 | 0.07, p = 0.258 |

TABLE 1-continued

Patient characteristics and survey scores by clinical and machine learning diagnostic clusters

| Variable | Clinical Diagnosis Groups 1 (n = 95) | 2 (n = 275) | 3 (n = 76) | 4 (n = 68) | Machine learning (ML) Diagnosis Groups 1 (n = 142) | 2 (n = 85) | 3 (n = 111) | 4 (n = 121) | 5 (n = 55) |
|---|---|---|---|---|---|---|---|---|---|
| GUPI1B | 0.04 | 0.26 | 0.46 | 0.36, p < 0.001 | 0.04 | 0.56 | 0.58 | 0.10 | 0.08, p = 0.846 |
| GUPI1C | 0.06 | 0.24 | 0.56 | 0.31, p < 0.001 | 0.03 | 0.54 | 0.62 | 0.10 | 0.08, p = 0.846 |
| GUPI1D | 0.13 | 0.39 | 0.89 | 0.56, p < 0.001 | 0.07 | 0.96 | 0.81 | 0.23 | 0.28, p = 0.405 |
| GUPI2A | 0.05 | 0.29 | 0.58 | 0.41, p < 0.001 | 0.04 | 0.69 | 0.62 | 0.10 | 0.18, p = 0.801 |
| GUPI2B | 0.14 | 0.21 | 0.51 | 0.46, p < 0.001 | 0.12 | 0.50 | 0.57 | 0.12 | 0.08, p = 0.212 |
| GUPI2C | 0.06 | 0.23 | 0.76 | 0.35, p < 0.001 | 0.02 | 0.77 | 0.52 | 0.09 | 0.23, p = 0.613 |
| GUPI2D | 0.12 | 0.24 | 0.65 | 0.38, p < 0.001 | 0.05 | 0.80 | 0.44 | 0.14 | 0.25, p = 0.685 |
| GUPI3 | 0.54 | 1.74 | 3.45 | 2.70, p < 0.001 | 0.55 | 3.90 | 3.20 | 1.01 | 1.65, p = 0.139 |
| GUPI4 | 0.99 | 2.81 | 5.71 | 4.30, p < 0.001 | 0.75 | 6.69 | 5.02 | 1.64 | 2.93, p = 0.073 |
| GUPI5 | 0.77 | 1.98 | 2.40 | 2.00, p < 0.001 | 0.48 | 3.71 | 1.68 | 2.15 | 1.94, p < 0.001 |
| GUPI6 | 1.58 | 2.54 | 3.35 | 2.81, p < 0.001 | 0.95 | 1.89 | 2.53 | 2.79 | 3.83, p < 0.001 |
| GUPI7 | 0.50 | 1.10 | 1.43 | 1.43, p < 0.001 | 0.20 | 2.02 | 1.29 | 0.63 | 2.11, p < 0.001 |
| GUPI8 | 0.79 | 1.86 | 2.43 | 2.32, p < 0.001 | 0.56 | 2.60 | 2.53 | 1.71 | 2.53, p < 0.001 |
| GUPI9 | 2.26 | 4.03 | 4.78 | 4.62, p < 0.001 | 2.06 | 5.22 | 4.72 | 3.75 | 5.21, p < 0.001 |
| PFD20_1 | 0.68 | 1.10 | 2.21 | 1.75, p < 0.001 | 0.54 | 2.24 | 1.83 | 0.94 | 1.25, p = 0.032 |
| PFD20_2 | 0.57 | 0.92 | 1.87 | 1.10, p < 0.001 | 0.42 | 1.97 | 1.48 | 0.67 | 0.95, p = 0.283 |
| PFD20_3 | 0.57 | 0.42 | 0.18 | 0.20, p < 0.001 | 0.43 | 0.47 | 0.28 | 0.32 | 0.47, p = 0.397 |
| PFD20_4 | 0.73 | 0.59 | 0.33 | 0.42, p = 0.008 | 0.52 | 0.86 | 0.26 | 0.52 | 0.88, p = 0.561 |
| PFD20_5 | 0.85 | 1.37 | 1.22 | 1.55, p = 0.003 | 0.63 | 2.03 | 0.99 | 1.61 | 1.62, p < 0.001 |
| PFD20_6 | 0.11 | 0.13 | 0.04 | 0.14, p = 0.932 | 0.07 | 0.25 | 0.04 | 0.09 | 0.21, p = 0.556 |
| PFD20_7 | 0.78 | 0.83 | 0.62 | 0.91, p = 0.683 | 0.57 | 1.27 | 0.65 | 0.70 | 1.17, p = 0.081 |
| PFD20_8 | 0.94 | 0.91 | 1.17 | 1.07, p = 0.162 | 0.71 | 1.45 | 0.91 | 1.03 | 0.92, p = 0.254 |
| PFD20_9 | 0.42 | 0.18 | 0.07 | 0.08, p < 0.001 | 0.22 | 0.30 | 0.05 | 0.08 | 0.53, p = 0.656 |
| PFD20_10 | 0.52 | 0.44 | 0.33 | 0.37, p = 1.74 | 0.32 | 0.64 | 0.25 | 0.25 | 1.15, p = 0.001 |
| PFD20_11 | 0.77 | 0.71 | 0.45 | 0.54, p = 0.037 | 0.55 | 0.79 | 0.44 | 0.62 | 1.27, p = 0.004 |
| PFD20_12 | 0.23 | 0.28 | 0.31 | 0.37, p = 0.134 | 0.14 | 0.65 | 0.25 | 0.27 | 0.22, p = 0.931 |
| PFD20_13 | 0.69 | 0.67 | 0.64 | 0.83, p = 0.355 | 0.47 | 1.17 | 0.50 | 0.63 | 1..05, p = 0.058 |
| PFD20_14 | 0.33 | 0.24 | 0.17 | 0.39, p = 0.530 | 0.24 | 0.57 | 0.09 | 0.23 | 0.32, p = 0.489 |
| PFD20_15 | 1.61 | 2.04 | 2.03 | 1.90, p = 0.351 | 1.08 | 2.52 | 1.72 | 2.26 | 3.06, p < 0.001 |
| PFD20_16 | 1.20 | 1.27 | 0.93 | 1.11, p = 0.254 | 0.71 | 1.38 | 0.65 | 1.44 | 2.65, p < 0.001 |
| PFD20_17 | 1.95 | 1.14 | 1.10 | 0.97, p < 0.001 | 1.27 | 1.37 | 0.83 | 1.23 | 2.00, p = 0.057 |
| PFD20_18 | 1.50 | 1.16 | 0.79 | 0.97, p = 0.002 | 0.98 | 1.17 | 0.60 | 1.20 | 2.49, p < 0.001 |
| PFD20_19 | 0.61 | 0.79 | 0.92 | 0.97, p = 0.028 | 0.39 | 1.45 | 0.69 | 0.93 | 0.79, p = 0.016 |
| PFD20_20 | 0.57 | 0.98 | 2.25 | 1.40, p < 0.001 | 0.40 | 2.40 | 1.91 | 0.57 | 0.91, p = 0.759 |

*Groups means reported for each group.

REFERENCES

1. Coyne K S, Sexton C C, Thompson C L et al. The prevalence of lower urinary tract symptoms (LUTS) in the USA, the UK and Sweden: results from the Epidemiology of LUTS (EpiLUTS) study. BJU Int 2009; 104: 352-60
2. Milsom I, Kaplan S A, Coyne K S, Sexton C C, Kopp Z S. Effect of bothersome overactive bladder symptoms on health-related quality of life, anxiety, depression, and treatment seeking in the United States: results from EpiLUTS. Urology 2012; 80: 90-6
3. Coyne K S, Wein A, Nicholson S, Kvasz M, Chen C I, Milsom I. Economic burden of urgency urinary incontinence in the United States: a systematic review. J Manag Care Pharm 2014; 20: 130-40
4. NIH. Meeeting on Measurement of Urinary Symptoms. Available at: http://www.niddk.nih.gov/news/events-calendar/Pages/meeting-on-measurement-of-urinary-symptoms-momus.aspx. Accessed November 2017
5. Hanno P M, Burks D A, Clemens J Q et al. AUA guideline for the diagnosis and treatment of interstitial cystitis/bladder pain syndrome. J Urol 2011; 185: 2162-70
6. Gormley E A, Lightner D J, Burgio K L et al. Diagnosis and treatment of overactive bladder (non-neurogenic) in adults: AUA/SUFU guideline. J Urol 2012; 188: 2455-63
7. Lai H H, Vetter J, Jain S, Gereau R W, Andriole G L. The overlap and distinction of self-reported symptoms between interstitial cystitis/bladder pain syndrome and overactive bladder: a questionnaire based analysis. J Urol 2014; 192: 1679-86
8. Erickson B J, Korfiatis P, Akkus Z, Kline T L. Machine Learning for Medical Imaging. Radiographics. 2017 March-April; 37(2):505-515.
9. Awan S E, Sohel F, Sanfilippo F M, Bennamoun M, Dwivedi G. Machine learning in heart failure: ready for prime time. Curr Opin Cardiol. 2018 March; 33(2): 190-195.
10. Awan S E, Sohel F, Sanfilippo F M, Bennamoun M, Dwivedi G. Machine learning in heart failure: ready for prime time. Curr Opin Cardiol. 2018 March; 33(2): 190-195.
11. Adamson A S, Welch H G. Machine Learning and the Cancer-Diagnosis Problem—No Gold Standard. N Engl J Med. 2019 Dec. 12; 381(24):2285-2287.
12. Obermeyer Z, Emanuel E J. Predicting the Future—Big Data, Machine Learning, and Clinical Medicine. N Engl J Med. 2016 Sep. 29; 375(13):1216-9.
13. Suarez-Ibarrola R, Hein S, Reis G, Gratzke C, Miernik A. Current and future applications of machine and deep learning in urology: a review of the literature on urolithiasis, renal cell carcinoma, and bladder and prostate cancer. World J Urol. 2019 Nov. 5.
14. Goldenberg S L, Nir G, Salcudean S E. A new era: artificial intelligence and machine learning in prostate cancer. Nat Rev Urol. 2019 July; 16(7):391-403.
15. Hasnain Z, Mason J, Gill K, Miranda G, Gill I S, Kuhn P, Newton P K. Machine learning models for predicting post-cystectomy recurrence and survival in bladder cancer patients. PLoS One. 2019 Feb. 20; 14(2)
16. Choo M S, Uhmn S, Kim J K, Han J H, Kim D H, Kim J, Lee S H. A Prediction Model Using Machine Learning Algorithm for Assessing Stone-Free Status after Single Session Shock Wave Lithotripsy to Treat Ureteral Stones. J Urol. 2018 December; 200(6):1371-1377.
17. Kocak B, Yardimci A H, Bektas C T, Turkcanoglu M R, Erdim C, Yucetas U, Koca S B, Kilickesmez O. Textural differences between renal cell carcinoma subtypes: Machine learning-based quantitative computed tomography texture analysis with independent external validation. Eur J Radiol. 2018 October; 107:149-157.
18. Ozkan I A, Koklu M, Sert I U. Diagnosis of urinary tract infection based on artificial intelligence methods. Comput Methods Programs Biomed. 2018 November; 166:51-59.
19. Sheyn D, Ju M, Zhang S, Anyaeche C, Hij az A, Mangel J, Mahaj an S, Conroy B, El-Nashar S, Ray S. Development and Validation of a Machine Learning Algorithm for Predicting Response to Anticholinergic Medications for Overactive Bladder Syndrome. Obstet Gynecol. 2019 November; 134(5):946-957.
20. Karmonik C, Boone T, Khavari R. Data-Driven Machine-Learning Quantifies Differences in the Voiding Initiation Network in Neurogenic Voiding Dysfunction in Women With Multiple Sclerosis. Int Neurourol J. 2019 September; 23(3):195-204.
21. Clemens J Q, Mullins C, Ackerman A L, Bavendam T, van Bokhoven A, Ellingson B M, Harte S E, Kutch J J, Lai H H, Martucci K T, Moldwin R, Naliboff B D, Pontari M A, Sutcliffe S, Landis J R; MAPP Research Network Study Group. Urologic chronic pelvic pain syndrome: insights from the MAPP Research Network. Nat Rev Urol. 2019 March; 16(3):187-200.
22. Ackerman A L, Lai H H, Parameshwar P S, Eilber K S, Anger J T. Symptomatic overlap in overactive bladder and interstitial cystitis/bladder pain syndrome: development of a new algorithm. BJU Int. 2019 April; 123 (4): 682-693.
23. Thu J H L, Vetter J, Lai H H. The Severity and Distribution of Nonurologic Pain and Urogenital Pain in Overactive Bladder are Intermediate Between Interstitial Cystitis and Controls. Urology. 2019 August; 130:59-64.
24. Biasi G, Di Sabatino V, Ghizzani A, Galeazzi M. Chronic pelvic pain: comorbidity between chronic musculoskeletal pain and vulvodynia. Reumatismo. 2014 Jun. 6; 66(1): 87-91.
25. Wolff B J, Joyce C J, Brincat C A, Mueller E R, Fitzgerald C M. Pelvic floor myofascial pain in patients with symptoms of urinary tract infection. Int J Gynaecol Obstet. 2019 May; 145(2):205-211.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A system for evaluating a patient, the system comprising:

a display device;

a user interface;

a memory; and a control system coupled to the memory and comprising one or more processors, the control system configured to execute a machine executable code stored thereon to cause the control system to:

display, on the display device, a series of questions from a set of one or more urinary tract health questionnaires;

receive, from the user interface, a selection of answers from the patient in response to the displayed series of questions, the answers being associated with one or more urinary tract symptoms of the patient;

process, using a first supervised machine learning model, the selection of answers to output a classification of the one or more urinary tract symptoms of the patient into a respective one of a plurality of diagnostic clusters, wherein the plurality of diagnostic clusters is generated by an unsupervised machine learning model trained according to a clustering algorithm to receive a plurality of training patient response datasets and categorize the plurality of training patient response datasets into the plurality of diagnostic clusters, wherein each of the plurality of diagnostic clusters is associated with a distinct urinary tract disease category, and wherein the first supervised machine learning model is trained on the plurality of training patient response datasets and the diagnostic cluster into which each training patient response dataset was categorized by the unsupervised machine learning model;

process, using a second supervised machine learning model, the selection of answers to output an initial severity level of the urinary tract disease category of the patient that is associated with the respective one of the plurality of diagnostic clusters, the second supervised machine learning model being specific to the respective one of the plurality of diagnostic clusters, the second machine learning model for each respective diagnostic cluster being trained on (i) a portion of the plurality of training patient response datasets categorized into the respective diagnostic cluster by the unsupervised machine learning model, and (ii) a set of corresponding severity level labels;

determine recommended treatments to be selectively administered to the patient that are specific to (i) the respective diagnostic cluster for the patient that is output by the first supervised machine learning model and (ii) the initial severity level of the urinary tract disease category of the patient associated with the respective diagnostic cluster that is output by the second supervised machine learning model;

administer a first of the recommended treatments in response to the respective diagnostic cluster for the patient being associated with bladder pain syndrome, wherein the administration of the first recommended treatment includes an intravesical instillation in the patient;

administer a second of the recommended treatments in response to the respective diagnostic cluster for the patient being associated with non-urological urogenital pain, wherein the administration of the second recommended treatment includes using an agent to cause placement of a topical anesthetic at a desired site;

administer a third of the recommended treatments in response to the respective diagnostic cluster for the patient being associated with pelvic floor dysfunction, wherein the administration of the third recommended treatment includes pelvic floor physical therapy being performed on the patient; and administer a fourth of the recommended treatments in response to the respective diagnostic cluster for the patient being associated with urgency urinary incontinence, wherein the administration of the fourth recommended treatment includes using the agent to cause placement of antimuscarinic and sympathomimetic oral medications at the desired site.

2. The system of claim 1, wherein the plurality of diagnostic clusters includes an asymptomatic control cluster, a bladder pain syndrome cluster, a non-urologic urogenital pain cluster, a pelvic floor dysfunction cluster, and an urgency urinary incontinence cluster.

3. The system of claim 1, wherein the first supervised machine learning model is trained using a training dataset, the training dataset comprising a plurality of patient response datasets, each of the plurality of patient response datasets including responses to the one or more urinary tract health questionnaires from one of a plurality of patients.

4. The system of claim 3, wherein the unsupervised machine learning model includes a k-means clustering algorithm, and wherein an elbow method is used to determine a number of the plurality of diagnostic clusters.

5. The system of claim 3, wherein the unsupervised machine learning model is trained based on one or more of a Ward's method of hierarchical clustering, an elbow method to determine a number of the plurality of diagnostic clusters, and a k-means clustering algorithm.

6. The system of claim 3, wherein the second supervised machine learning model is a classification model or a regression model.

7. The system of claim 6, wherein the second supervised machine learning model is a random forest model.

8. The system of claim 1, wherein the control system is further configured to execute the machine executable code to cause the control system to predict an effectiveness of each of the recommended treatments based on the classification.

9. The system of claim 1, wherein the set of one or more urinary tract health questionnaires comprises one or more of Interstitial Cystitis Symptom and Problem Indices (ICSI/ICPI), Overactive Bladder Questionnaire (OABq), Genitourinary Pain Index (GUPI), and Pelvic Floor Disability Index (PFDI-20).

10. The system of claim 1, wherein the first supervised machine learning model is a random forest model, and wherein the random forest model is trained using a dataset labelled using an unsupervised k-means clustering process on data from the set of one or more urinary tract health questionnaires.

11. The system of claim 1, wherein the control system is further configured to execute the machine executable code to cause the control system to:
store the first supervised machine learning model in the memory;
train the first supervised machine learning model with the selection of answers from the patient and demographic data to output an updated first supervised machine learning model; and
store the updated first supervised machine learning model in the memory.

12. The system of claim 1, wherein the classification of the one or more urinary tract symptoms of the patient into the respective one of the plurality of diagnostic clusters is further based on a set of demographic data describing the patient.

13. The system of claim 1, wherein the initial severity level is determined at a first time, and wherein the control system is further configured to execute the machine executable code to, at a second time after the first time subsequent to the patient being administered the recommended treatment:
display, on the display device, the series of questions from the set of one or more urinary tract health questionnaires;
receive, from the user interface, an updated selection of answers from the patient in response to the displayed series of questions; and
determine whether to update the recommended treatment based on a difference between the severity level determined at the first time and an updated severity level determined at the second time.

14. A method for evaluating a patient, the method comprising:
receiving, via a user interface, a set of patient response data for the patient associated with one or more urinary tract symptoms of the patient;
processing the set of patient response data using a first supervised machine learning model to output a classification of the one or more urinary tract symptoms of the patient into a respective one of a plurality of diagnostic clusters, wherein the plurality of diagnostic clusters is generated by an unsupervised machine learning model, and wherein each of the plurality of diagnostic clusters is associated with a distinct urinary tract disease category;
processing the set of patient response data using a second supervised machine learning model to output an initial severity level of the urinary tract disease category of the patient that is associated with the respective one of the plurality of diagnostic clusters, the second supervised machine learning model being specific to the respective one of the plurality of diagnostic clusters; and
determining recommended treatments to be selectively administered to the patient that are specific to (i) the respective diagnostic cluster for the patient that is output by the first supervised machine learning model and (ii) the initial severity level of the urinary tract disease category of the patient associated with the respective diagnostic cluster that is output by the second supervised machine learning model;
administering a first of the recommended treatments in response to the respective diagnostic cluster for the patient being associated with bladder pain syndrome, wherein the administration of the first recommended treatment includes an intravesical instillation in the patient;
administering a second of the recommended treatments in response to the respective diagnostic cluster for the patient being associated with non-urological urogenital pain, wherein the administration of the second recommended treatment includes a topical anesthetic at a desired site;
administering a third of the recommended treatments in response to the respective diagnostic cluster for the patient being associated with pelvic floor dysfunction, wherein the administration of the recommended treatment includes pelvic floor physical therapy being performed on the patient, a trigger point injection being performed on the patient, using an agent to cause placement of a muscle relaxant at the desired site, performing a pelvic floor biofeedback treatment, or any combination thereof; and
administering a fourth of the recommended treatments in response to the respective diagnostic cluster for the patient being associated with urgency urinary incontinence, wherein the administration of the fourth recommended treatment includes using the agent to cause placement of antimuscarinic and sympathomimetic oral medications at the desired site.

15. The method of claim 14, wherein the unsupervised machine learning model includes a k-means clustering algorithm, wherein a number of the plurality of diagnostic clusters is determined according to an elbow method, and wherein the first supervised machine learning model is a random forest model.

16. The method of claim 14, wherein the second supervised machine learning model is trained to output a severity level for each classification determined by the first supervised machine learning model.

17. The method of claim 14, wherein the plurality of diagnostic clusters includes an asymptomatic control cluster, a bladder pain syndrome cluster, a non-urologic urogenital pain cluster, a pelvic floor dysfunction cluster, and an urgency urinary incontinence cluster.

18. The method of claim 14, wherein the set of patient response data is based on patient responses to one or more urinary tract health questionnaires, the one or more urinary tract health questionnaires comprising one or more of Interstitial Cystitis Symptom and Problem Indices (ICSI/ICPI), Overactive Bladder Questionnaire (OABq), Genitourinary Pain Index (GUPI), and Pelvic Floor Disability Index (PFDI-20).

19. The method of claim 14, wherein the initial severity level is determined at a first time, and wherein the method further comprises, at a second time after the first time subsequent to the patient being administered the recommended treatment:
displaying, on a display device, a series of questions from the set of one or more urinary tract health questionnaires;
receiving, from the user interface, an updated selection of answers from the patient in response to the displayed series of questions; and
determining whether to update the recommended treatment based on a difference between the severity level determined at the first time and an updated severity level determined at the second time.

20. A system comprising:

a memory;

a control system comprising one or more processors coupled to the memory, the memory storing executable code, a first supervised machine learning model, and a second supervised machine learning model, the control system configured to execute the executable code to cause the control system to:

receive a set of patient data associated with one or more urinary tract symptoms of the patient;

process, using the first supervised machine learning model, the set of patient data to output a classification of the one or more urinary tract symptoms of the patient into a respective one of a plurality of diagnostic clusters, wherein the plurality of diagnostic clusters is generated by an unsupervised machine learning model, and wherein each of the plurality of diagnostic clusters is associated with a distinct urinary tract disease category;

process the set of patient data using a second supervised machine learning model to output an initial severity level of the urinary tract disease category of the patient that is associated with the respective one of the plurality of diagnostic clusters, the second supervised machine learning model being specific to the respective one of the plurality of diagnostic clusters; and determining recommended treatments to be selectively administered to the patient that are specific to (i) the respective diagnostic cluster for the patient that is output by the first supervised machine learning model and (ii) the initial severity level of the urinary tract disease category of the patient associated with the respective diagnostic cluster that is output by the second supervised machine learning model;

administering a first of the recommended treatments in response to the respective diagnostic cluster for the patient being associated with bladder pain syndrome, wherein the administration of the first recommended treatment includes an intravesical instillation in the patient; and administering a second of the recommended treatments in response to the respective diagnostic cluster for the patient being associated with non-urological urogenital pain, wherein the administration of the second recommended treatment includes using an agent to cause placement of a topical anesthetic at a desired site;

in response to the respective diagnostic cluster for the patient being associated with pelvic floor dysfunction, the recommended treatment includes pelvic floor physical therapy; and in response to the respective diagnostic cluster for the patient being associated with urgency urinary incontinence, the recommended treatment includes antimuscarinic and sympathomimetic oral medications;

after a first administration of the recommended treatment, re-evaluating the patient by acquiring an updated selection of answers to a series of questions from one or more urinary tract health questionnaires and reprocessing the updated selection of answers with the second supervised machine learning model to determine an updated severity level of the urinary tract disease category of the patient that is associated with the respective one of the plurality of diagnostic clusters; and automatically updating the recommended treatment in response to a difference between the initial severity level and the updated severity level.

21. The system of claim 20, wherein the plurality of diagnostic clusters includes an asymptomatic control cluster, a bladder pain syndrome cluster, a non-urologic urogenital pain cluster, a pelvic floor dysfunction cluster, and an urgency urinary incontinence cluster.

22. The system of claim 20, wherein the unsupervised machine learning model includes a k-means clustering algorithm, and wherein an elbow method is used to determine a number of the plurality of diagnostic clusters.

23. The system of claim 20, wherein the second supervised machine learning model is a classification model or a regression model, wherein the control system is further configured to execute the executable code to cause the control system to:

administer a third of the recommended treatments in response to the respective diagnostic cluster for the patient being associated with pelvic floor dysfunction, wherein the administration of the third recommended treatment includes pelvic floor physical therapy being performed on the patient.

24. The system of claim 23, wherein the second supervised machine learning model is a random forest model, wherein the control system is further configured to execute the executable code to cause the control system to: administer a fourth of the recommended treatments in response to the respective diagnostic cluster for the patient being associated with urgency urinary incontinence, wherein the administration of the fourth recommended treatment includes using the agent to cause placement of antimuscarinic and sympathomimetic oral medications at the desired site.

25. The system of claim 20, wherein the set of patient data is based on are based on patient responses to a set of one or more urinary tract health questionnaires, the one or more urinary tract health questionnaires comprising one or more of Interstitial Cystitis Symptom and Problem Indices (ICSI/ICPI), Overactive Bladder Questionnaire (OABq), Genitourinary Pain Index (GUPI), and Pelvic Floor Disability Index (PFDI-20).

26. The system of claim 20, wherein the initial severity level is determined at a first time, and wherein the control system is further configured to execute the executable code to, at a second time after the first time subsequent to the patient being administered the recommended treatment:

receive an updated set of patient data for the patient associated with the one or more urinary tract symptoms of the patient; and determine whether to update the recommended treatment based on a difference between the severity level determined at the first time and the updated severity level determined at the second time.

* * * * *